(12) United States Patent
Ophardt et al.

(10) Patent No.: US 11,980,328 B2
(45) Date of Patent: May 14, 2024

(54) FOAM DISPENSER WITH IONIC WIND DRIVEN OZONE GENERATION AND AIR CIRCULATION

(71) Applicant: OP-Hygiene IP GmbH, Niederbipp (CH)

(72) Inventors: Heiner Ophardt, Arisdorf (CH); Andrew Jones, St. Anns (CA)

(73) Assignee: OP-HYGIENE IP GMBH, Niederbipp (CH)

( * ) Notice: Subject to any disclaimer, the term of this patent is extended or adjusted under 35 U.S.C. 154(b) by 867 days.

(21) Appl. No.: 17/070,303

(22) Filed: Oct. 14, 2020

(65) Prior Publication Data

US 2021/0106182 A1    Apr. 15, 2021

Related U.S. Application Data

(60) Provisional application No. 62/915,151, filed on Oct. 15, 2019.

(51) Int. Cl.
| | | |
|---|---|---|
| *A47K 5/14* | (2006.01) | |
| *A61L 2/20* | (2006.01) | |
| *C01B 13/11* | (2006.01) | |

(52) U.S. Cl.
CPC ............ *A47K 5/14* (2013.01); *A61L 2/202* (2013.01); *C01B 13/11* (2013.01)

(58) Field of Classification Search
CPC .... A47K 5/00; A47K 5/14; A61L 2/00; A61L 2/16; A61L 2/20; A61L 2/202; B05B 7/00; B05B 7/0018; B05B 7/0025; B05B 7/0031; B05B 7/0037; B05B 11/00; B05B 11/01; B05B 11/10; B05B 11/1087; C01B 13/00; C01B 13/10; C01B 13/11
See application file for complete search history.

(56) References Cited

U.S. PATENT DOCUMENTS

| | | |
|---|---|---|
| 3,638,058 A | 1/1972 | Fritzius |
| 4,643,745 A | 2/1987 | Sakakibara et al. |
| (Continued) | | |

FOREIGN PATENT DOCUMENTS

| | | |
|---|---|---|
| EP | 2662008 A2 | 11/2013 |
| JP | 2001 009252 | 1/2001 |

OTHER PUBLICATIONS

Machine translation of JP 2001009252 A, provided in IDS filed on May 24, 2021 and published on Jan. 16, 2001. (Year: 2001).*

*Primary Examiner* — Natasha E Young
(74) *Attorney, Agent, or Firm* — Thorpe North & Western, LLP

(57) ABSTRACT

A dispenser for dispensing ozone containing foam. The dispenser comprises an ozone generating chamber having an air inlet in communication with a source of air and an air outlet. The ozone generating chamber contains a corona discharge generator that generates a corona discharge to produce: (a) ozonated air, by converting oxygen in the air into ozone, and (b) an ionic wind. The ionic wind draws the air from the air source into the ozone generating chamber through the air inlet, and expels the ozonated air from the ozone generating chamber through the air outlet. A foam generator receives the ozonated air expelled from the ozone generating chamber and mixes the ozonated air with a foamable liquid to generate the ozone containing foam.

16 Claims, 14 Drawing Sheets

(56) References Cited

U.S. PATENT DOCUMENTS

| | | | |
|---|---|---|---|
| 4,689,056 A * | 8/1987 | Noguchi | B03C 3/12 96/79 |
| 6,508,982 B1 | 1/2003 | Shoji | |
| 7,911,146 B2 | 3/2011 | Dunn-Rankin et al. | |
| 8,063,382 B2 | 11/2011 | MacDonald et al. | |
| 8,272,539 B2 | 9/2012 | Ophardt | |
| 8,672,187 B2 | 3/2014 | Ophardt | |
| 8,733,596 B2 | 5/2014 | Ophardt | |
| 9,620,936 B2 | 4/2017 | Katano | |
| 9,936,841 B2 * | 4/2018 | Ophardt | A47K 5/1217 |
| 10,124,083 B2 | 11/2018 | Robert | |
| 2003/0072675 A1 | 4/2003 | Takeda et al. | |
| 2006/0112955 A1 | 6/2006 | Reaves | |
| 2013/0119083 A1 | 5/2013 | Ophardt | |
| 2013/0232807 A1 | 9/2013 | Robert et al. | |
| 2020/0223693 A1 | 7/2020 | Ophardt | |

\* cited by examiner

FOAM DISPENSER WITH IONIC WIND DRIVEN OZONE GENERATION AND AIR CIRCULATION

CROSS-REFERENCE TO RELATED APPLICATIONS

This application claims the benefit of the filing date of U.S. Provisional Patent Application Ser. No. 62/915,151 to Ophardt et al., filed Oct. 15, 2019, which is incorporated herein by reference.

FIELD OF THE INVENTION

This invention relates to hand cleaning foam dispensers, and more particularly to dispensers that dispense ozone containing foam.

BACKGROUND OF THE INVENTION

Dispensers that dispense ozone containing hand cleaning foam are known in the art. For example, U.S. Pat. No. 8,733,596 to Ophardt et al., issued May 27, 2014, which is incorporated herein by reference, teaches the use of ultraviolet radiation or corona discharges to generate ozone from the oxygen in air. The resulting ozonated air is then passed through a foam generator together with a suitable foamable liquid to generate the ozone containing foam. The ozone containing foam can be dispensed onto a user's hand, for example, with the ozone providing a sanitizing effect.

The inventors of the present invention have appreciated that known dispensers for dispensing ozone containing foam suffer a number of disadvantages. For example, at least some of the previously known dispensers incorporate an ozone generating chamber that contains an ozone generator and a relatively static volume of air. When ozone is generated by the ozone generator within the static volume of air, there is a risk that the concentration of ozone may not be consistent throughout the entire volume of air. For example, the air located near the ozone generator may have a higher concentration of ozone than the air located further away from the ozone generator. This variability in the ozone concentration could potentially cause a number of problems. For example, it may be difficult to accurately determine the overall concentration of ozone within the chamber using an ozone detecting sensor or the like, since the concentration of ozone near the sensor could differ significantly from the concentration of ozone elsewhere within the chamber. Furthermore, the amount of ozone that is dispensed with each activation of the dispenser could vary, depending on the concentration of ozone in the volume of air that gets delivered to the foam generator.

Another problem with some previously known dispensers is that there is a delay after a user activates the dispenser before the ozone containing foam is dispensed, which can be frustrating for the user. This can occur, for example, when the dispenser has an air chamber that receives the ozonated air from the ozone generating chamber during a recharging stroke, and then delivers the ozonated air to the foam generator during a dispensing stroke. Because the ozone naturally decomposes into oxygen over time, the air chambers of prior art dispensers generally cannot store a supply of ozonated air in between activations. Instead, upon activation of the dispenser by the user, the dispenser must first generate a suitable quantity of ozone within the ozone generating chamber, and then draw the ozonated air into the air chamber in the recharging stroke, before finally delivering the ozonated air from the air chamber to the foam generator in the dispensing stroke.

SUMMARY OF THE INVENTION

To at least partially overcome some of the disadvantages of previously known methods and devices, in one aspect the present invention provides a dispenser having an ozone generating chamber with an air inlet in communication with a source of air and an air outlet, the ozone generating chamber containing a corona discharge generator that generates a corona discharge to produce: (a) ozonated air, by converting oxygen in the air into ozone, and (b) an ionic wind that draws the air from the air source into the ozone generating chamber through the air inlet, and expels the ozonated air from the ozone generating chamber through the air outlet. The inventors have appreciated that an ionic wind can advantageously be used to circulate air into and out of the ozone generating chamber. In preferred embodiments, this allows the dispenser to operate without requiring separate pump mechanisms to draw air into and out of the ozone generating chamber, thus reducing the number of components in the dispenser and possibly reducing energy consumption.

Optionally, the air inlet and the air outlet are both in fluid communication with an air compartment, and the air compartment is in fluid communication with a foam generator for delivering the ozonated air from the air compartment to the foam generator. This configuration allows the ionic wind to circulate air between the air compartment and the ozone generating chamber, by drawing air from the air compartment into the ozone generating chamber through the air inlet, and expelling ozonated air from the ozone generating chamber back into the air compartment through the air outlet. The circulation of air and ozonated air between the ozone generating chamber and the air compartment provides the ozone generating chamber with a source of air for generating ozone, and also provides ozonated air to the air compartment, preferably in a well-mixed and uniformly concentrated state, where it is available for delivery to the foam generator for generating the ozone containing foam. Using the ionic wind to deliver the ozonated air to the air compartment allows the air compartment to be maintained in a charged state in between activations, with a supply of ozonated air contained in the air compartment and ready to be discharged when needed, thus reducing or eliminating the delay between the activation of the dispenser and the dispensing of the ozone containing foam. In addition, having both the air circulation and the ozone generation functions provided by the corona discharge reduces the number of components that are required.

In another aspect, the present invention provides a dispenser with an ozone generating chamber having an air inlet and an air outlet, the ozone generating chamber having an ozone generator that produces ozonated air inside the ozone generating chamber by converting oxygen in air into ozone; an air compartment that contains a supply of air and is in fluid communication with the air inlet and the air outlet; and an air flow generator that circulates the air from the air compartment into the ozone generating chamber through the air inlet, and circulates the ozonated air from the ozone generating chamber into the air compartment through the air outlet. The inventors have appreciated that by providing an air flow generator that circulates the air between the ozone generating chamber and the air compartment, the air compartment can be maintained in a charged state in between activations, with a supply of ozonated air contained in the air compartment and ready to be discharged when needed, thus reducing or eliminating the delay between the activation of the dispenser and the dispensing of the ozone containing foam. The ozone generator is preferably a corona discharge generator that also functions as the air flow generator by producing an ionic wind. Other suitable air flow generators such as conventional fans or air pumps could also be used.

In a further aspect, the present invention provides a dispenser with an ozone generating chamber having a corona discharge generator that generates a corona discharge to produce: (a) ozonated air, by converting oxygen in air into ozone, and (b) an ionic wind that circulates the ozonated air. The inventors have appreciated that by configuring the corona discharge generator to produce an ionic wind, the ionic wind can advantageously be used to circulate and mix the generated ozone. The ionic wind can thus preferably be used to provide a uniform concentration of ozone within the ozone generating chamber and/or within an air compartment in fluid communication with the ozone generating chamber. Having a uniform concentration of ozone can improve the functioning of the dispenser by, for example, allowing the concentration of ozone to be accurately detected by an ozone sensor and/or by providing a consistent concentration of ozone to be dispensed with each activation of the dispenser.

Accordingly, in a first aspect the present invention provides a dispenser for dispensing ozone containing foam, the dispenser comprising: an ozone generating chamber having an air inlet in communication with a source of air and an air outlet, the ozone generating chamber containing a corona discharge generator that generates a corona discharge to produce: (a) ozonated air, by converting oxygen in the air into ozone, and (b) an ionic wind that draws the air from the air source into the ozone generating chamber through the air inlet, and expels the ozonated air from the ozone generating chamber through the air outlet; a foam generator that receives the ozonated air expelled from the ozone generating chamber and mixes the ozonated air with a foamable liquid to generate the ozone containing foam; and a discharge outlet for discharging the ozone containing foam.

In a second aspect the present invention provides a dispenser, which optionally incorporates one or more features of the first aspect, wherein the air moves through the ozone generating chamber in an air flow path from the air inlet to the air outlet; wherein the corona discharge generator comprises a first electrode and a second electrode, the first electrode positioned upstream from the second electrode in the air flow path; wherein the first electrode produces ions that are attracted to the second electrode; and wherein the ionic wind is generated by movement of the ions from the first electrode towards the second electrode.

In a third aspect, the present invention provides a dispenser, which optionally incorporates one or more features of any one or more of the first and second aspects, the dispenser further comprising a desiccant that is positioned between the air inlet and the first electrode.

In a fourth aspect, the present invention provides a dispenser, which optionally incorporates one or more features of any one or more of the first to third aspects, further comprising a desiccant that is positioned between the air inlet and the first electrode; wherein the first electrode and the second electrode provide air flow passages that allow air to flow past the first electrode and past the second electrode to generate the ionic wind; wherein the first electrode and the second electrode each comprise a plurality of elongated electrode members; and wherein the air flow passages are defined between the elongated electrode members.

In a fifth aspect, the present invention provides a dispenser, which optionally incorporates one or more features of any one or more of the first to fourth aspects, further comprising an air compartment that is in fluid communication with the air outlet for receiving the ozonated air from the ozone generating chamber, the air compartment in fluid communication with the foam generator for delivering the ozonated air from the air compartment to the foam generator.

In a sixth aspect, the present invention provides a dispenser, which optionally incorporates one or more features of any one or more of the first to fifth aspects, further comprising: a reservoir containing a supply of the foamable liquid; a liquid pump for delivering the foamable liquid from the reservoir to the foam generator; and an air pump for delivering the ozonated air from the air compartment to the foam generator.

In a seventh aspect, the present invention provides a dispenser, which optionally incorporates one or more features of any one or more of the first to sixth aspects, wherein the air pump selectively decreases a volume of the air compartment to force at least some of the ozonated air from the air compartment into the foam generator.

In an eighth aspect, the present invention provides a dispenser, which optionally incorporates one or more features of any one or more of the first to seventh aspects, wherein the air compartment is the source of air that is in fluid communication with the air inlet; and wherein the ionic wind circulates air and ozonated air between the air compartment and the ozone generating chamber from the air compartment into the ozone generating chamber through the air inlet, and from the ozone generating chamber into the air compartment through the air outlet.

In a ninth aspect, the present invention provides a dispenser, which optionally incorporates one or more features of any one or more of the first to eighth aspects, wherein the air compartment is the source of air that is in fluid communication with the air inlet; and wherein the ionic wind circulates air and ozonated air between the air compartment and the ozone generating chamber in an air flow path from the air compartment into the ozone generating chamber through the air inlet, and from the ozone generating chamber into the air compartment through the air outlet.

In a tenth aspect, the present invention provides a dispenser, which optionally incorporates one or more features of any one or more of the first to eighth aspects, wherein the air compartment is the source of air that is in fluid communication with the air inlet; and wherein the ionic wind circulates air and ozonated air between the air compartment and the ozone generating chamber in the air flow path from the air compartment into the ozone generating chamber through the air inlet, and from the ozone generating chamber into the air compartment through the air outlet.

In an eleventh aspect, the present invention provides a dispenser, which optionally incorporates one or more features of any one or more of the first to tenth aspects, wherein the dispenser comprises a piston forming body and a piston chamber forming element; wherein the piston forming body is slidable along a piston axis relative to the piston chamber forming element between an extended position and a retracted position; wherein the piston chamber forming element has an air chamber forming portion that defines an air chamber; wherein the piston forming body has an air displacement portion that is received within the air chamber; wherein the air compartment is at least partially defined between the air displacement portion and the air chamber forming portion; and wherein axial movement of the air displacement portion relative to the air chamber forming portion during a dispensing stroke decreases the volume of the air compartment, which forces at least some of the ozonated air from the air compartment into the foam generator.

In a twelfth aspect, the present invention provides a dispenser, which optionally incorporates one or more features of any one or more of the first to eleventh aspects, further comprising a one-way air inlet valve that allows atmospheric air to enter the air compartment through the one-way air inlet valve, and that prevents the air from exiting the air compartment through the one-way air inlet valve; wherein axial movement of the air displacement portion relative to the air chamber forming portion during a recharging stroke increases the volume of the air compartment, which generates a vacuum within the air compartment that draws the atmospheric air into the air compartment through the one-way air inlet valve.

In a thirteenth aspect, the present invention provides a dispenser, which optionally incorporates one or more features of any one or more of the first to twelfth aspects, wherein the piston chamber forming element has a liquid chamber forming portion that defines a liquid chamber; wherein the piston forming body has a liquid displacement portion that is received within the liquid chamber; wherein a liquid compartment is at least partially defined between the liquid displacement portion and the liquid chamber forming portion; the dispenser further comprising a one-way liquid inlet valve that allows the foamable liquid to enter the liquid compartment from the reservoir through the one-way liquid inlet valve, and that prevents the foamable liquid from exiting the liquid compartment through the one-way liquid inlet valve; wherein axial movement of the liquid displacement portion relative to the liquid chamber forming portion during the recharging stroke increases a volume of the liquid compartment, which generates a vacuum within the liquid compartment that draws the foamable liquid from the reservoir into the liquid compartment through the one-way liquid inlet valve; and wherein axial movement of the liquid displacement portion relative to the liquid chamber forming portion during the dispensing stroke decreases the volume of the liquid compartment, which forces at least some of the foamable liquid from the liquid compartment into the foam generator.

In a fourteenth aspect, the present invention provides a dispenser, which optionally incorporates one or more features of any one or more of the first to thirteenth aspects, wherein the liquid chamber forming portion comprises an inner wall of the piston chamber forming element, the inner wall having an inner surface and an outer surface; wherein the liquid compartment is at least partially defined between the inner surface of the inner wall and the liquid displacement portion; wherein the air chamber forming portion comprises an outer wall of the piston chamber forming element that is spaced radially outwardly from the inner wall; wherein the air compartment is at least partially defined between the outer surface of the inner wall, the air displacement portion, and the outer wall; and wherein the ozonated air expelled from the air outlet into the air compartment is directed into a curved circulation path around the outer surface of the inner wall.

In a fifteenth aspect, the present invention provides a dispenser, which optionally incorporates one or more features of any one or more of the first to fourteenth aspects, further comprising a one-way air outlet valve that allows the ozonated air to enter the foam generator from the air compartment through the one-way air outlet valve, and that prevents fluid from entering the air compartment from the foam generator through the one-way air outlet valve.

In a sixteenth aspect, the present invention provides a dispenser, which optionally incorporates one or more features of any one or more of the first to fifteenth aspects, further comprising a sensor that senses a concentration of ozone in the ozone generating chamber or in the air compartment, or that senses a parameter for estimating or calculating the concentration of ozone in the ozone generating chamber or in the air compartment.

In a seventeenth aspect, the present invention provides a dispenser, which optionally incorporates one or more features of any one or more of the first to sixteenth aspects, further comprising a controller that controls the corona discharge generator so that the concentration of ozone in the ozone generating chamber or in the air compartment is within a preselected range of concentrations.

In an eighteenth aspect, the present invention provides a dispenser, which optionally incorporates one or more features of any one or more of the first to seventeenth aspects, wherein the dispenser is a hand cleaner dispenser for dispensing the ozone containing foam onto a person's hand and the ozone containing foam is a hand cleaning foam.

In a nineteenth aspect, the present invention provides a dispenser, which optionally incorporates one or more features of any one or more of the first to eighteenth aspects, wherein the air moves through the ozone generating chamber in the air flow path from the air inlet to the air outlet; wherein the corona discharge generator comprises a first electrode and a second electrode, the first electrode positioned upstream from the second electrode in the air flow path; wherein the first electrode produces ions that are attracted to the second electrode; and wherein the ionic wind is generated by movement of the ions from the first electrode towards the second electrode.

In a twentieth aspect, the present invention provides a dispenser, which optionally incorporates one or more features of any one or more of the first to nineteenth aspects, wherein the first electrode and the second electrode provide air flow passages that allow air to flow past the first electrode and past the second electrode to generate the ionic wind.

In a twenty first aspect, the present invention provides a dispenser, which optionally incorporates one or more features of any one or more of the first to twentieth aspects, wherein the first electrode and the second electrode each comprise a plurality of elongated electrode members; and wherein the air flow passages are defined between the elongated electrode members.

In a twenty second aspect, the present invention provides a dispenser, which optionally incorporates one or more features of any one or more of the first to twenty first aspects, wherein the air moves through the ozone generating chamber in the air flow path from the air inlet to the air outlet; wherein the corona discharge generator comprises a first electrode and a second electrode, the first electrode positioned upstream from the second electrode in the air flow path; wherein the first electrode produces ions that are attracted to the second electrode; wherein the ionic wind is generated by movement of the ions from the first electrode towards the second electrode; wherein the first electrode and the second electrode provide air flow passages that allow air to flow past the first electrode and past the second electrode to generate the ionic wind; wherein the first electrode and the second electrode each comprise a plurality of elongated electrode members; wherein the air flow passages are defined between the elongated electrode members; and wherein the dispenser further comprises a desiccant that is positioned between the air inlet and the first electrode.

In a twenty third aspect, the present invention provides a dispenser, which optionally incorporates one or more features of any one or more of the first to twenty second aspects, further comprising: a sensor that senses a concentration of ozone in the ozone generating chamber or in the air compartment, or that senses a parameter for estimating or calculating the concentration of ozone in the ozone generating chamber or in the air compartment; and a controller that controls the corona discharge generator so that the concentration of ozone in the ozone generating chamber or in the air compartment is within a preselected range of concentrations; wherein the dispenser is a hand cleaner dispenser for dispensing the ozone containing foam onto a person's hand and the ozone containing foam is a hand cleaning foam.

In a twenty fourth aspect, the present invention provides a dispenser for dispensing ozone containing foam, which optionally incorporates one or more features of any one or more of the first to twenty third aspects, the dispenser comprising: an ozone generating chamber having an air inlet and an air outlet, the ozone generating chamber having an ozone generator that generates ozonated air inside the ozone generating chamber by converting oxygen in air into ozone; an air compartment that contains a supply of air and is in fluid communication with the air inlet and the air outlet; an air flow generator that circulates air and ozonated air between the air compartment and the ozone generating chamber in an air flow path from the air compartment into the ozone generating chamber through the air inlet, and from the ozone generating chamber into the air compartment through the air outlet; a foam generator that receives the ozonated air from the air compartment and mixes the ozonated air with a foamable liquid to generate the ozone containing foam; and a discharge outlet for discharging the ozone containing foam.

In a twenty fifth aspect, the present invention provides a dispenser, which optionally incorporates one or more features of any one or more of the first to twenty fourth aspects, wherein the ozone generator comprises a corona discharge generator that generates a corona discharge to produce: (a) the ozonated air, and (b) an ionic wind that draws the air from the air compartment into the ozone generating chamber through the air inlet, and expels the ozonated air from the ozone generating chamber into the air compartment through the air outlet; and wherein the air flow generator comprises the corona discharge generator.

In a twenty sixth aspect, the present invention provides a dispenser, which optionally incorporates one or more features of any one or more of the first to twenty fifth aspects, wherein the air moves through the ozone generating chamber in the air flow path from the air inlet to the air outlet; wherein the corona discharge generator comprises a first electrode and a second electrode, the first electrode positioned upstream from the second electrode in the air flow path; wherein the first electrode produces ions that are attracted to the second electrode; and wherein the ionic wind is generated by movement of the ions from the first electrode towards the second electrode.

In a twenty seventh aspect, the present invention provides a dispenser, which optionally incorporates one or more features of any one or more of the first to twenty sixth aspects, further comprising a desiccant that is positioned between the air inlet and the first electrode.

In a twenty eighth aspect, the present invention provides a dispenser, which optionally incorporates one or more features of any one or more of the first to twenty seventh aspects, further comprising an air inlet opening for delivering atmospheric air to the air compartment to replenish the supply of air.

In a twenty ninth aspect, the present invention provides a dispenser, which optionally incorporates one or more features of any one or more of the first to twenty eighth aspects, further comprising: a reservoir containing a supply of the foamable liquid; a liquid pump for delivering the foamable liquid from the reservoir to the foam generator; and an air pump for delivering the ozonated air from the air compartment to the foam generator.

In a thirtieth aspect, the present invention provides a dispenser, which optionally incorporates one or more features of any one or more of the first to twenty ninth aspects, wherein the air pump selectively decreases a volume of the air compartment to force at least some of the ozonated air from the air compartment into the foam generator.

In a thirty first aspect, the present invention provides a dispenser, which optionally incorporates one or more features of any one or more of the first to thirtieth aspects, wherein the dispenser comprises a piston forming body and a piston chamber forming element; wherein the piston forming body is slidable along a piston axis relative to the piston chamber forming element between an extended position and a retracted position; wherein the piston chamber forming element has an air chamber forming portion that defines an air chamber; wherein the piston forming body has an air displacement portion that is received within the air chamber; wherein the air compartment is at least partially defined between the air displacement portion and the air chamber forming portion; and wherein axial movement of the air displacement portion relative to the air chamber forming portion during a dispensing stroke decreases the volume of the air compartment, which forces at least some of the ozonated air from the air compartment into the foam generator.

In a thirty second aspect, the present invention provides a dispenser, which optionally incorporates one or more features of any one or more of the first to thirty first aspects, further comprising a one-way air inlet valve that allows atmospheric air to enter the air compartment through the one-way air inlet valve, and that prevents the air from exiting the air compartment through the one-way air inlet valve; and wherein axial movement of the air displacement portion relative to the air chamber forming portion during a recharging stroke increases the volume of the air compartment, which generates a vacuum within the air compartment that draws the atmospheric air into the air compartment through the one-way air inlet valve.

In a thirty third aspect, the present invention provides a dispenser, which optionally incorporates one or more features of any one or more of the first to thirty second aspects, wherein the piston chamber forming element has a liquid chamber forming portion that defines a liquid chamber; wherein the piston forming body has a liquid displacement portion that is received within the liquid chamber; wherein a liquid compartment is at least partially defined between the liquid displacement portion and the liquid chamber forming portion; the dispenser further comprising a one-way liquid inlet valve that allows the foamable liquid to enter the liquid compartment from the reservoir through the one-way liquid inlet valve, and that prevents the foamable liquid from exiting the liquid compartment through the one-way liquid inlet valve; wherein axial movement of the liquid displacement portion relative to the liquid chamber forming portion during the recharging stroke increases a volume of the liquid compartment, which generates a vacuum within the liquid compartment that draws the foamable liquid from the reservoir into the liquid compartment through the one-way liquid inlet valve; and wherein axial movement of the liquid displacement portion relative to the liquid chamber forming portion during the dispensing stroke decreases the volume of the liquid compartment, which forces at least some of the foamable liquid from the liquid compartment into the foam generator.

In a thirty fourth aspect, the present invention provides a dispenser, which optionally incorporates one or more features of any one or more of the first to thirty third aspects, wherein the liquid chamber forming portion comprises an inner wall of the piston chamber forming element, the inner wall having an inner surface and an outer surface; wherein the liquid compartment is at least partially defined between the inner surface of the inner wall and the liquid displacement portion; wherein the air chamber forming portion comprises an outer wall of the piston chamber forming element that is spaced radially outwardly from the inner wall; wherein the air compartment is at least partially defined between the outer surface of the inner wall, the air displacement portion, and the outer wall; and wherein the ozonated air expelled from the air outlet into the air compartment is directed into a curved circulation path around the outer surface of the inner wall.

In a thirty fifth aspect, the present invention provides a dispenser, which optionally incorporates one or more features of any one or more of the first to thirty fourth aspects, further comprising a one-way air outlet valve that allows the ozonated air to enter the foam generator from the air compartment through the one-way air outlet valve, and that prevents fluid from entering the air compartment from the foam generator through the one-way air outlet valve.

In a thirty sixth aspect, the present invention provides a dispenser, which optionally incorporates one or more features of any one or more of the first to thirty fifth aspects, further comprising a sensor that senses a concentration of ozone in the ozone generating chamber or in the air compartment, or that senses a parameter for estimating or calculating the concentration of ozone in the ozone generating chamber or in the air compartment.

In a thirty seventh aspect, the present invention provides a dispenser, which optionally incorporates one or more features of any one or more of the first to thirty sixth aspects, further comprising a controller that controls the ozone generator so that the concentration of ozone in the ozone generating chamber or in the air compartment is within a preselected range of concentrations.

In a thirty eighth aspect, the present invention provides a dispenser, which optionally incorporates one or more features of any one or more of the first to thirty seventh aspects, wherein the dispenser is a hand cleaner dispenser for dispensing the ozone containing foam onto a person's hand and the ozone containing foam is a hand cleaning foam.

In a thirty ninth aspect, the present invention provides a dispenser for dispensing ozone containing foam, which optionally incorporates one or more features of any one or more of the first to thirty eighth aspects, the dispenser comprising: an ozone generating chamber having a corona discharge generator that generates a corona discharge to produce: (a) ozonated air, by converting oxygen in air into ozone, and (b) an ionic wind that circulates the ozonated air; a foam generator that receives the ozonated air and mixes the ozonated air with a foamable liquid to generate the ozone containing foam; and a discharge outlet for discharging the ozone containing foam; wherein the corona discharge generator comprises a first electrode and a second electrode; wherein the first electrode produces ions that are attracted to the second electrode; and wherein the ionic wind is generated by movement of the ions from the first electrode towards the second electrode.

In a fortieth aspect, the present invention provides a dispenser, which optionally incorporates one or more features of any one or more of the first to thirty ninth aspects, wherein the dispenser comprises an air compartment for delivering the ozonated air to the foam generator; and wherein the first electrode and the second electrode are positioned so that the ionic wind circulates the ozonated air to provide a substantially uniform ozone concentration within the air compartment.

In a forty first aspect, the present invention provides a dispenser, which optionally incorporates one or more features of any one or more of the first to fortieth aspects, wherein the ozone generating chamber at least partially defines the air compartment; and wherein the corona discharge generator is located within the air compartment.

In a forty second aspect, the present invention provides a dispenser, which optionally incorporates one or more features of any one or more of the first to forty first aspects, wherein the first electrode and the second electrode provide air flow passages that allow air to flow past the first electrode and past the second electrode to generate the ionic wind.

In a forty third aspect, the present invention provides a dispenser, which optionally incorporates one or more features of any one or more of the first to forty second aspects, wherein the first electrode and the second electrode each comprise a plurality of elongated electrode members; and wherein the air flow passages are defined between the elongated electrode members.

In a forty fourth aspect, the present invention provides a dispenser, which optionally incorporates one or more features of any one or more of the first to forty first aspects, wherein the dispenser is a hand cleaner dispenser for dispensing the ozone containing foam onto a person's hand and the ozone containing foam is a hand cleaning foam.

BRIEF DESCRIPTION OF THE DRAWINGS

Further aspects and advantages of the invention will appear from the following description taken together with the accompanying drawings, most of which are in a computer generated format often known as wire-frame images with hidden-line removal, in which, simplistically stated, lines are shown where there is a change in the plane of a surface, and in which.

DETAILED DESCRIPTION OF THE DRAWINGS

Figure 1:
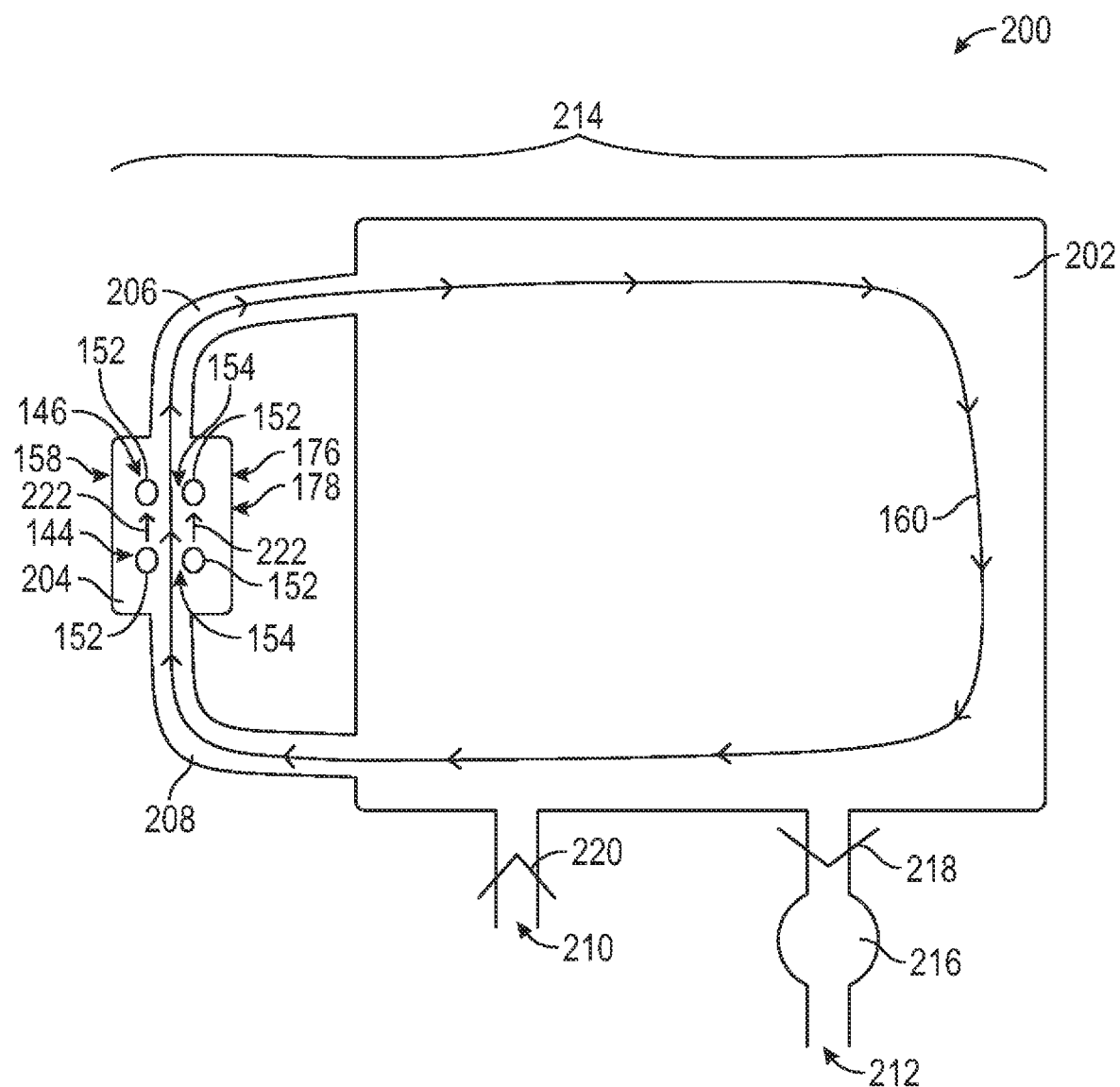
FIG. 1 is a schematic representation of an ozone generation and storage device in accordance with a first embodiment of the present invention.

FIG. 1 shows a schematic representation of an ozone generation and storage device 200 in accordance with a first embodiment of the present invention. The device 200 has a storage compartment 202, an ozone generation compartment 204, a first fluid circulation tube 206, and a second fluid circulation tube 208. The storage compartment 202 has a fluid inlet 210 and a fluid outlet 212. Together, the storage compartment 202, the ozone generation compartment 204, and the two fluid circulation tubes 206, 208 define an internal ozone circulation compartment 214 that is sealed from the external environment, other than at the fluid inlet 210 and the fluid outlet 212.

The fluid outlet 212 has a fluid pump 216 that is configured to pump fluid from the internal ozone circulation compartment 214 out through the fluid outlet 212. A one-way fluid outlet valve 218 allows the fluid to be pumped out of the internal ozone circulation compartment 214 through the fluid outlet 212, and prevents fluid from entering the internal ozone circulation compartment 214 through the fluid outlet 210.

The fluid inlet 210 is in fluid communication with a source of an oxygen containing gas, preferably atmospheric air. A one-way fluid inlet valve 220 allows the atmospheric air to enter the internal ozone circulation compartment 214 through the fluid inlet 210, and prevents fluid from exiting the internal ozone circulation compartment 214 through the fluid inlet 210.

The ozone generation compartment 204 contains a first electrode 144 and a second electrode 146. The first electrode 144 and the second electrode 146 each have two electrode members 152 that are spaced from each other with an air passage 154 therebetween. Together, the first electrode 144 and the second electrode 146 function as a corona discharge generator 158.

The ozone generation and storage device 200 is configured to generate ozone, and to circulate the ozone throughout the internal ozone circulation compartment 214 so that the concentration of ozone within the internal ozone circulation compartment 214 is substantially uniform. Before the ozone is generated, atmospheric air enters the device 200 through the fluid inlet 210 and fills the internal ozone circulation compartment 214. The corona discharge generator 158 is then activated by applying a sufficiently high voltage between the first electrode 144 and the second electrode 146 to generate a corona discharge. As is known in the art, the corona discharge generates ozone from the oxygen in the atmospheric air to produce ozonated air.

The corona discharge also produces ions in the air adjacent to the first electrode 144. The ions are attracted to the second electrode 146, and so move from the first electrode 144 towards the second electrode 146, as shown by the arrows 222 in FIG. 1. As the ions travel from the first electrode 144 towards the second electrode 146, they collide with air molecules in the atmospheric air, propelling the air molecules towards the second electrode 146. This generates a flow of air from the first electrode 144 towards the second electrode 146. The flow of air generated by the movement of the ions is referred to herein as an ionic wind.

As the air molecules propelled by the ions are not themselves attracted to the second electrode 146, when the air molecules reach the second electrode 146 they do not stop, but rather continue flowing through the air passage 154 and the first fluid circulation tube 206 into the storage compartment 202. At the same time, the movement of air away from the first electrode 144 towards the second electrode 146 generates a local vacuum beside the first electrode 144, which draws air from the storage compartment 202 into the ozone generation compartment 204 through the second fluid circulation tube 208. The ionic wind thus propels the air in a circular air flow path 160 that circulates and recirculates the air between the storage compartment 202 and the ozone generation compartment 204.

The corona discharge generator 158 thus functions as both an ozone generator 176 and an air flow generator 178, with the ozone that is generated by the corona discharge being circulated throughout the internal ozone circulation compartment 214 by the ionic wind. Preferably, the circulation of the ozone by the ionic wind provides a substantially uniform concentration of ozone throughout the internal ozone circulation compartment 214.

The internal ozone circulation compartment 214 serves as a reservoir of ozonated air available to be discharged from the fluid outlet 212 when needed by activation of the fluid pump 216. When the ozonated air is discharged from the fluid outlet 212, atmospheric air is then drawn into the internal ozone circulation compartment 214 through the fluid inlet 210, to replace the discharged ozonated air. More ozone can then be generated from the oxygen in the atmospheric air by activating the corona discharge generator 158.

Advantageously, if the concentration of ozone stored within the internal ozone circulation compartment 214 decreases over time due to the natural decomposition of the ozone back into oxygen, the corona discharge generator 158 can be reactivated to generate and circulate more ozone as needed. This additional ozone is generated from the oxygen in the air that is already contained in the internal ozone circulation compartment 214. The device 200 is thus able to recycle the air, rather than requiring the air to be discarded and replaced every time the ozone naturally decomposes.

Although the ozone generation and storage device 200 shown in FIG. 1 is depicted as having a separate storage compartment 202 and ozone generation compartment 204, which are connected by fluid circulation tubes 206, 208, this is not necessary. For example, in the second embodiment of the invention shown in FIG. 2, wherein like numerals are used to denote like components, the ozone generation and storage functions are all performed within a single internal ozone circulation compartment 214 that is not divided into a separate storage compartment 202 and ozone generation compartment 204. The ozone generation and storage device 200 shown in FIG. 2 functions in the same manner as the device 200 shown in FIG. 1, with the only difference being that the air circulated within the internal ozone circulation compartment 214 by the ionic wind does not pass through a distinct storage compartment 202, ozone generation compartment 204, or fluid circulation tubes 206, 208.

Figure 2:
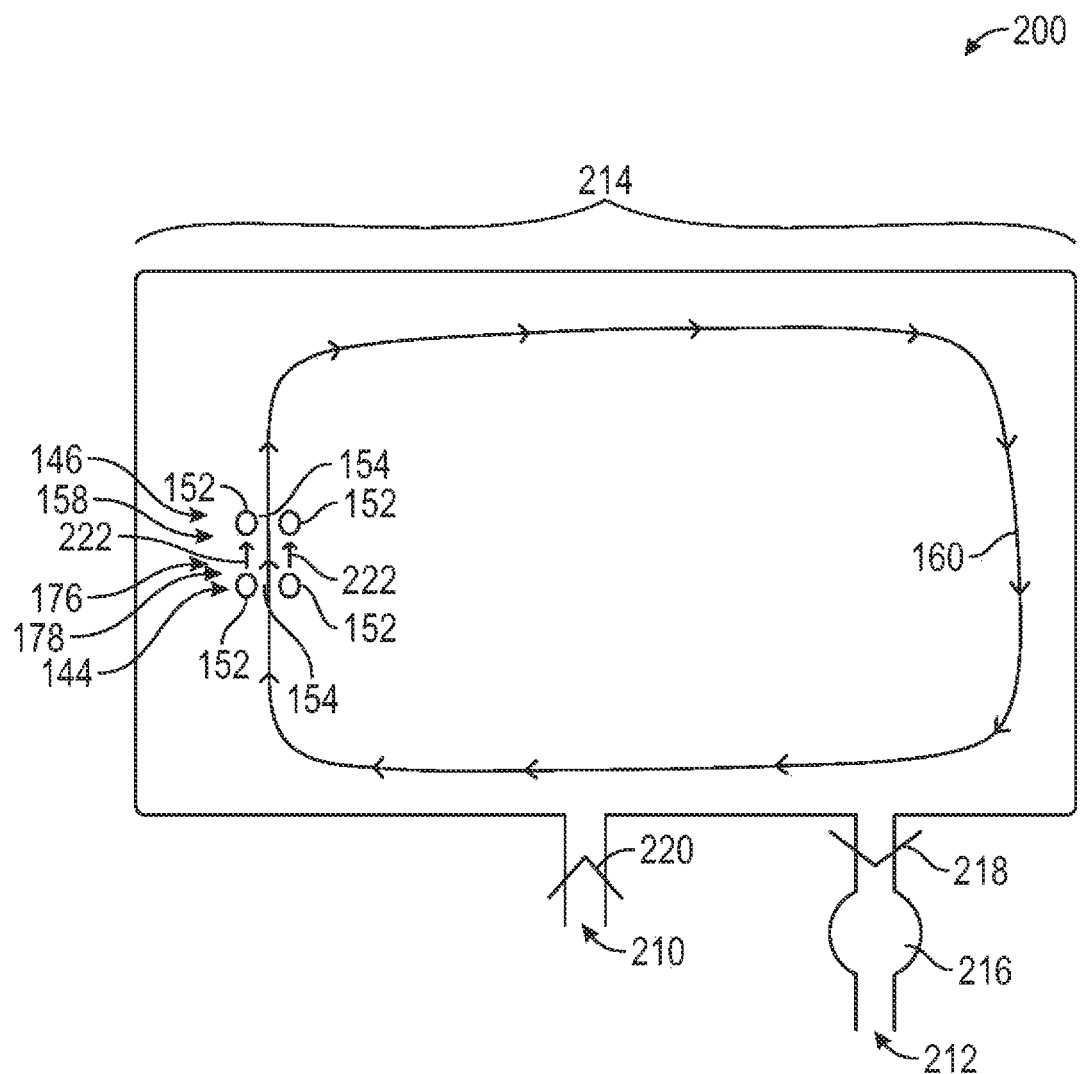
FIG. 2 is a schematic representation of an ozone generation and storage device in accordance with a second embodiment of the present invention.

The ozone generation and storage devices 200 shown schematically in FIGS. 1 and 2 could be used to generate ozonated air for any desired purpose. The ozonated air could, for example, be used to generate an ozone containing foam for disinfecting a person's hands, as in the third embodiment of the invention shown in FIGS. 3 to 11 and described below, wherein like numerals are used to denote like components.

Figure 3:
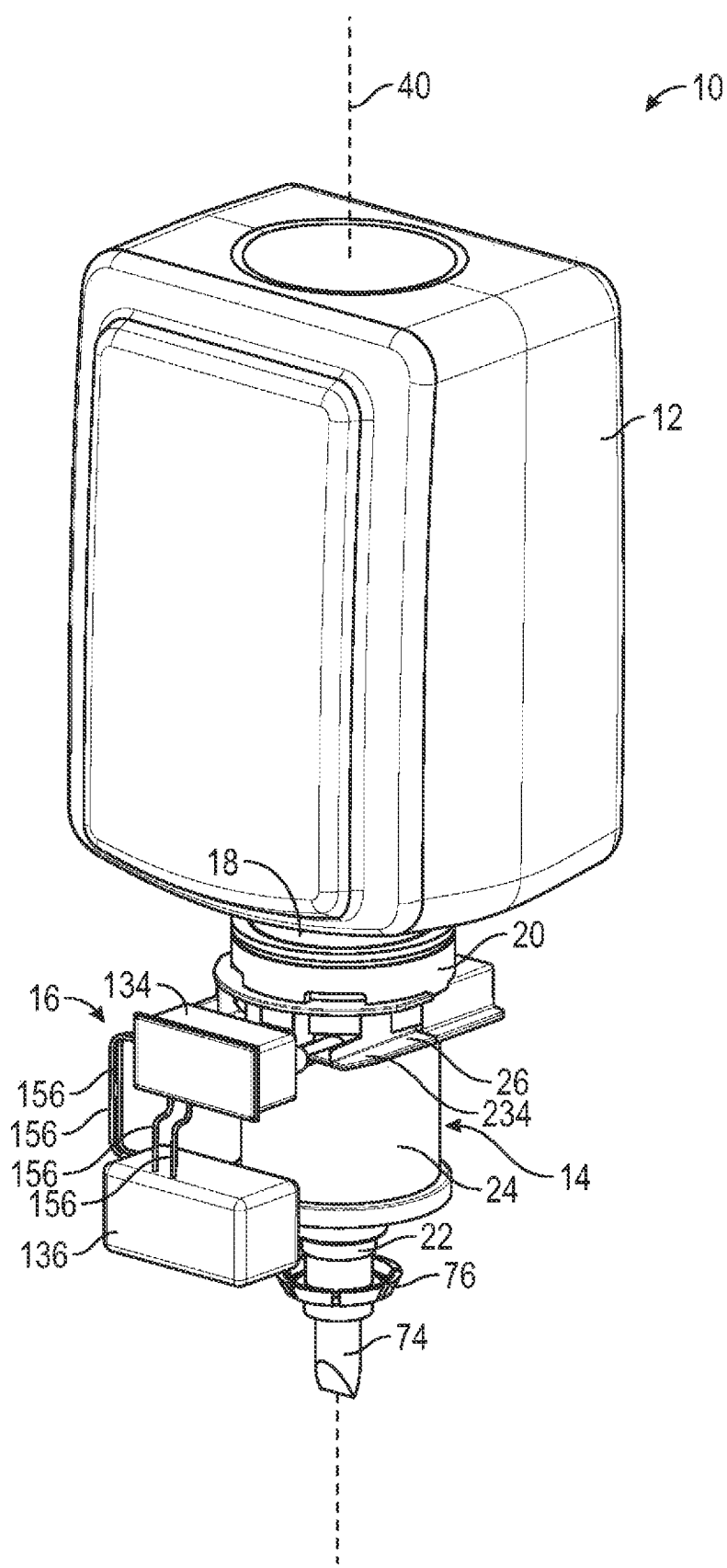
FIG. 3 is a rear perspective view of a foam dispenser in accordance with a third embodiment of the present invention.

FIG. 3 shows a foam dispenser 10 in accordance with the third embodiment of the present invention. The foam dispenser 10 has a fluid reservoir 12, a piston pump 14, and an ozone generation assembly 16. The fluid reservoir 12 is a plastic bottle that contains a foamable liquid, such as hand soap or hand sanitizer. The reservoir 12 has a neck portion 18 with an open end, not shown, that is received by a reservoir engagement portion 20 of the piston pump 14 for delivering the foamable liquid from the reservoir 12 to the piston pump 14.

Figure 4:
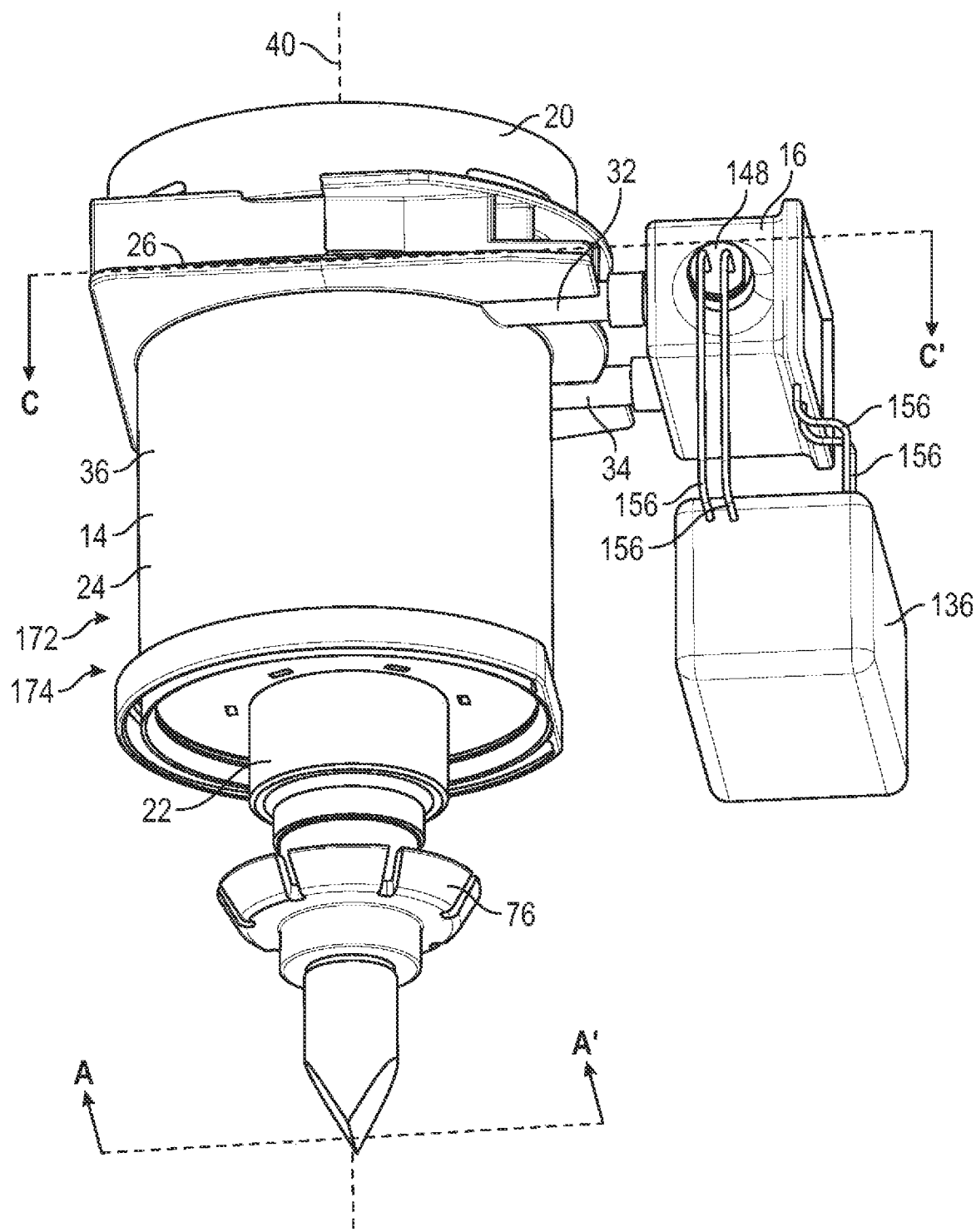
FIG. 4 is a bottom perspective view of a piston pump and an ozone generation assembly of the foam dispenser of FIG. 3.
Figure 5:
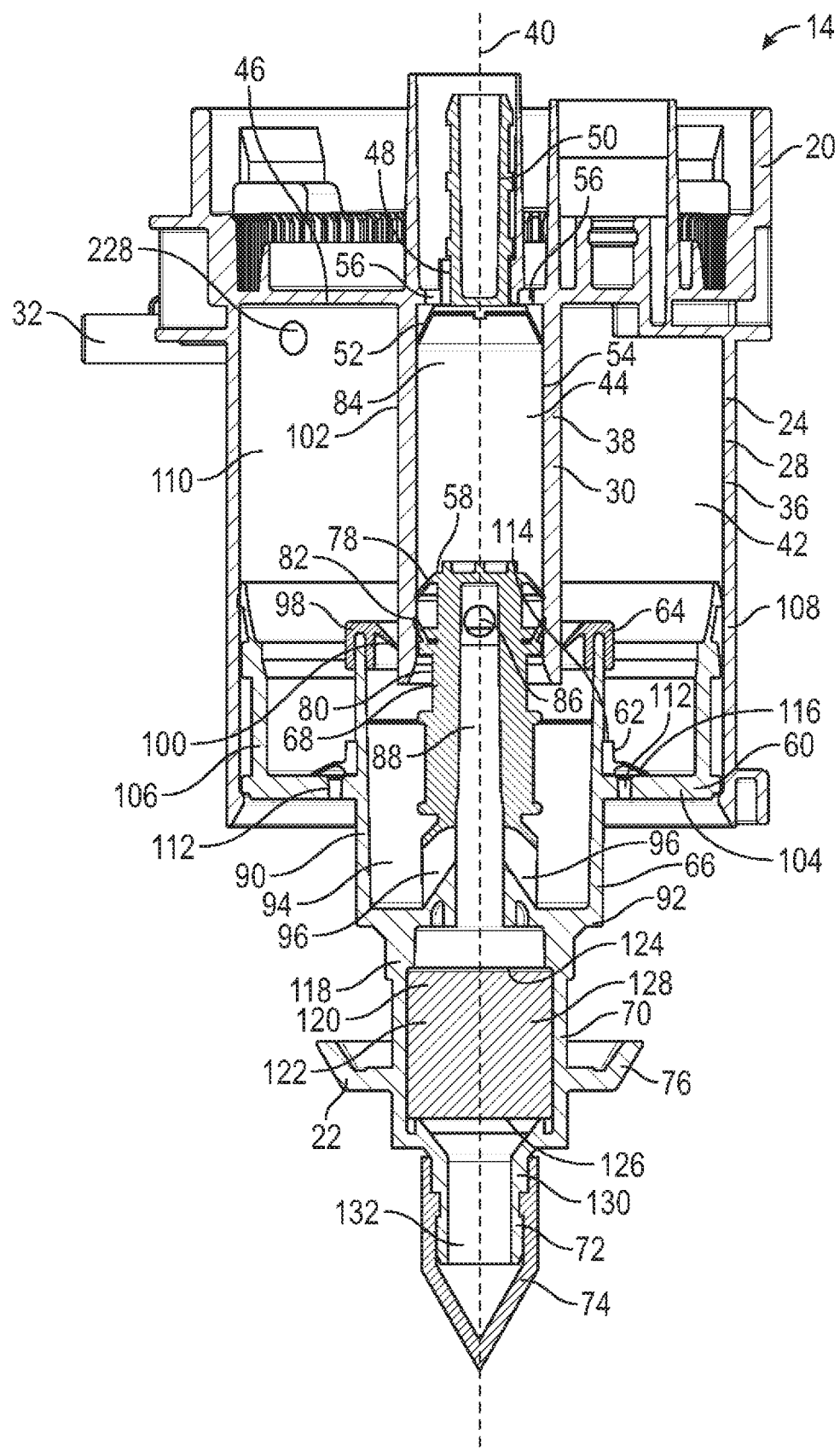
FIG. 5 is a left side cross-sectional view of the piston pump shown in FIG. 4, taken along line A-A' in FIG. 4, and showing the piston pump in an extended position.

As can be seen in FIGS. 4 and 5, the piston pump 14 has a piston forming body 22 and a piston chamber forming element 24. In addition to the reservoir engagement portion 20 mentioned above, the piston chamber forming element 24 also has a housing engagement portion 26, an air chamber forming portion 28, a liquid chamber forming portion 30, an air inlet tube 32, and an air outlet tube 34. The housing engagement portion 26 is formed by two horizontal mounting flanges 234 that extend from the front of the piston pump 14 to the back of the piston pump 14. The mounting flange 234 on the left side of the piston pump 14 is best shown in FIG. 3, and the mounting flange 234 on the right side of the piston pump 14 is best shown in FIG. 4. As is known in the art, the mounting flanges 234 are configured to be received by corresponding mounting slots in a dispenser housing, not shown, for fixing the vertical position of the piston chamber forming element 24 relative to the housing.

As best shown in FIG. 5, the reservoir engagement portion 20 has a partition wall 46 that extends generally horizontally across the bottom of the reservoir engagement portion 20. A cylindrical outer wall 36 and a cylindrical inner wall 38 extend downwardly from the partition wall 46, the cylindrical outer wall 36 forming the air chamber forming portion 28 and the cylindrical inner wall 38 forming the liquid chamber forming portion 30. The cylindrical outer wall 36 and the cylindrical inner wall 38 are arranged concentrically about a piston axis 40, with the cylindrical outer wall 36 being spaced radially outwardly from the cylindrical inner wall 38. An air chamber 42 having an open bottom end is defined by the cylindrical outer wall 36, the partition wall 46, and an outer surface 102 of the cylindrical inner wall 38, and a liquid chamber 44 having an open bottom end is defined by the partition wall 46 and an inner surface 54 of the cylindrical inner wall 38. The air chamber 42 concentrically surrounds the liquid chamber 44.

The partition wall 46 has a central opening 48 that carries a one-way liquid inlet valve 50. The one-way liquid inlet valve 50 has a resiliently deformable disc 52 that engages with the inner surface 54 of the inner wall 38 when the disc 52 is in an unbiased state. Two liquid inlet openings 56 extend through the partition wall 46 adjacent to the central opening 48 for delivering the foamable liquid from the reservoir 12 to the liquid chamber 44.

Figure 11:
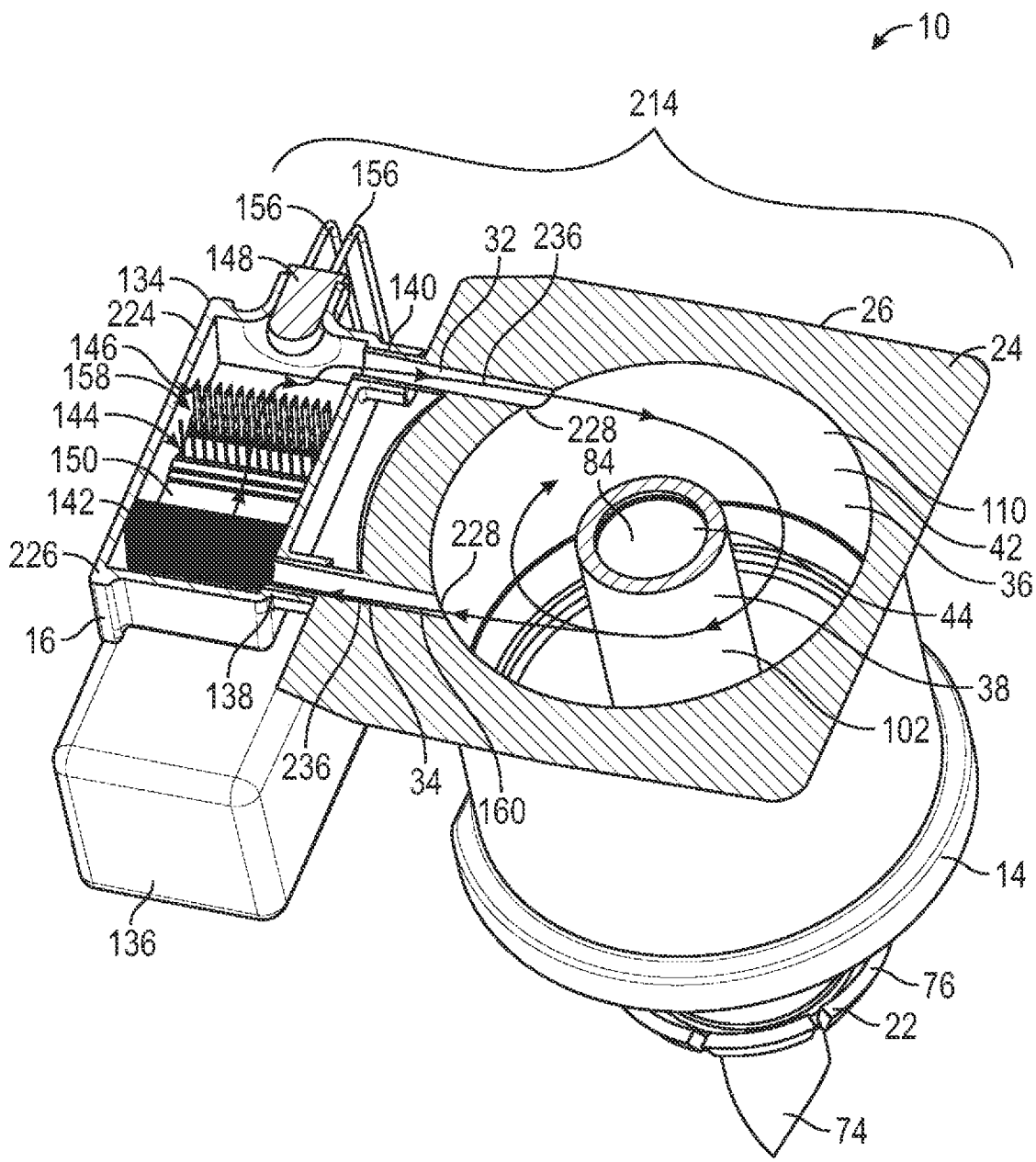
FIG. 11 is a top cross-sectional view of the piston pump and the ozone generation assembly shown in FIG. 4, taken along line C-C' in FIG. 4.

The air inlet tube 32 and the air outlet tube 34 are best shown in FIG. 4 as being cylindrical tubes that extend rearwardly from the outer wall 36 of the air chamber forming portion 28 for engagement with the ozone generation assembly 16. As can be seen in FIG. 11, the air inlet tube 32 and the air outlet tube 34 each define an inner passageway 236 with an inner open end 228 that opens into the air chamber 42 and places the inner passageway 236 in fluid communication with the air chamber 42.

As shown in FIG. 5, the piston forming body 22 has a liquid displacement portion 58, an air displacement portion 60, a one-way air inlet valve 62, a one-way air outlet valve 64, an outer air channel forming portion 66, a central stem 80, a foam chamber forming portion 70, a discharge outlet forming portion 72, a one-way foam outlet valve 74, and an engagement member 76. The liquid displacement portion 58 is positioned at the axially inner end of the central stem 80 of the piston forming body 22, and is received within the open bottom end of the liquid chamber 44. The liquid displacement portion 58 has a deformable disc member 78 that engages with the inner surface 54 of the inner wall 38 when in an unbiased condition. A sealing disc 82 is positioned axially outwardly from the deformable disc member 78, and also engages with the inner surface of the inner wall 38. A variable volume liquid compartment 84 is defined between the resiliently deformable disc 52 of the one-way liquid inlet valve 50, the inner surface 54 of the inner wall 38, and the deformable disc member 78 of the liquid displacement portion 58. The liquid displacement portion 58 is axially slidable within the liquid chamber 44 between the extended position shown in FIG. 5 and the retracted position shown in FIG. 7 to change the volume of the liquid compartment 84 and to function as a liquid pump 172.

The central stem 80 has a liquid receiving opening 86 that is positioned between the deformable disc member 78 and the sealing disc 82. The liquid receiving opening 86 opens into an inner liquid channel 88 that extends axially outwardly through the center of the central stem 80. The central stem 80 is also referred to herein as the inner liquid channel forming portion 68, because it carries the inner liquid channel 88.

The outer air channel forming portion 66 comprises a cylindrical piston wall 90 that is spaced radially outwardly from the central stem 80, and an attachment wall 92 that extends radially outwardly from the central stem 80 to attach the cylindrical piston wall 90 to the central stem 80. An outer air channel 94 is defined between the cylindrical piston wall 90 and the central stem 80. Two air introduction channels 96 extend through the central stem 80 to provide fluid communication between the outer air channel 94 and the inner liquid channel 88.

The one-way air outlet valve 64 comprises a ring-shaped cap member 98 that is positioned on an axially inner end of the cylindrical piston wall 90. The cap member 98 has a resiliently deformable inner rim 100 that sealingly engages with the outer surface 102 of the inner wall 38 when in an unbiased condition.

The air displacement portion 60 is received by the open bottom end of the air chamber 42 and comprises a ring-shaped radial extension wall 104 that extends radially outwardly from the cylindrical piston wall 90, and a generally cylindrical side wall 106 that extends axially inwardly from a radially distal portion of the radial extension wall 104. The side wall 106 has a sealing edge 108 that sealingly engages with the outer wall 36 of the piston chamber forming element 24. A variable volume air compartment 110 is defined between the air displacement portion 60, the outer wall 36, the partition wall 46, the inner wall 38, and the one-way air outlet valve 64. The air displacement portion 60 is axially slidable within the air chamber 42 between the extended position shown in FIG. 5 and the retracted position shown in FIG. 7 to change the volume of the air compartment 110 and to function as an air pump 174.

The radial extension wall 104 has multiple air inlet openings 112 that extend through the radial extension wall 104 to place the air compartment 110 in fluid communication with the surrounding atmospheric air. The one-way air inlet valve 62 comprises a ring-shaped attachment body 114 that circumferentially surrounds the cylindrical piston wall 90 adjacent to where the radial extension wall 104 meets the cylindrical piston wall 90. The ring-shaped attachment body 114 has a resiliently deformable ring-shaped flange 116 that extends radially outwardly from the ring-shaped attachment body 114, so that the ring-shaped flange 116 covers the axially inner ends of the air inlet openings 112. When in an unbiased condition, the radially outer edge of the ring-shaped flange 116 sealingly engages with the radial extension wall 104 to prevent air from exiting the air compartment 110 through the air inlet openings 112.

The foam chamber forming portion 70 comprises a generally cylindrical foam chamber forming wall 118 that extends axially outwardly from the attachment wall 92 of the outer air channel forming portion 66. The foam chamber forming wall 118 defines a foam chamber 120 that is in fluid communication with the axially outer end of the inner liquid channel 88. The foam chamber 120 contains a foam generator 122 for generating foam from the air and foamable liquid received from the inner liquid channel 88. In the embodiment shown, the foam generator 122 includes a first screen 124, a second screen 126, and a porous foaming sponge or plug 128. The first screen 124 extends radially across the foam chamber 120 near the axially inner end of the foam chamber 120, and the second screen 126 extends radially across the foam chamber 120 near the axially outer end of the foam chamber 120. The foaming sponge 128 is positioned between the first screen 124 and the second screen 126.

The discharge outlet forming portion 72 comprises a discharge outlet forming wall 130 that extends axially outwardly from the foam chamber forming portion 70. The discharge outlet forming wall 130 defines a discharge outlet 132 that is in fluid communication with the foam chamber 120 for discharging the foam generated by the foam generator 122. The one-way foam outlet valve 74 is attached to the discharge outlet forming wall 130, and is configured to allow the foam to exit the discharge outlet 132, and to prevent fluid from entering the discharge outlet 132 through the one-way foam outlet valve 74. In the embodiment shown, the one-way foam outlet valve 74 is a duckbill type valve, although other types of one-way valves could be used instead.

The engagement member 76 extends radially outwardly from the foam chamber forming wall 118. The engagement member 76 has an umbrella-like structure for engaging with a suitable pump actuator of a dispenser housing, not shown. As is known in the art, the engagement member 76 is used to effect axial movement of the piston forming body 22 relative to the piston chamber forming element 24, through engagement of the engagement member 76 with a pump actuator.

Figure 9:
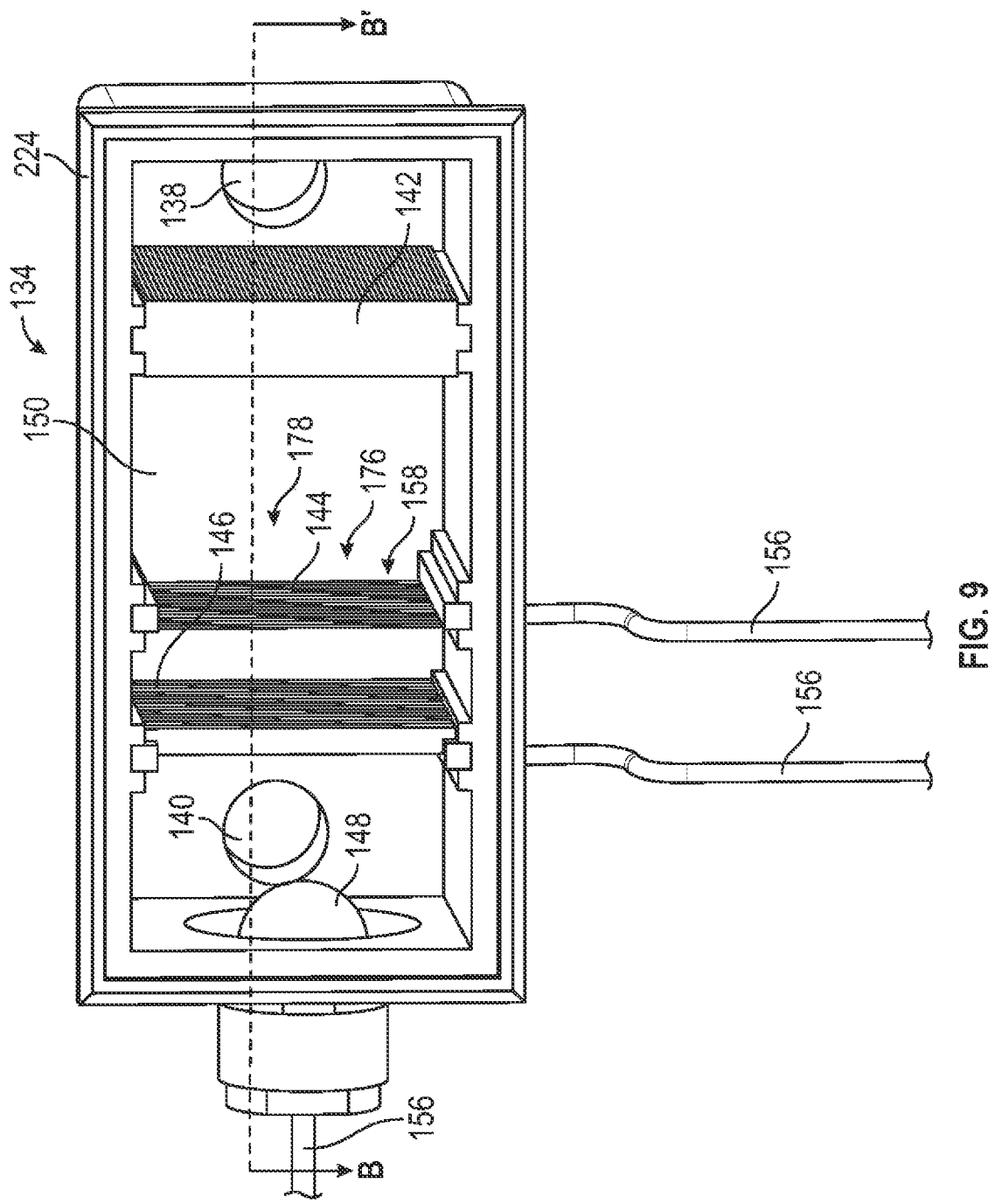
FIG. 9 is a rear perspective view of an ozone generating chamber of the dispenser shown in FIG. 3, with a rear cover of the ozone generating chamber removed.
Figure 10:
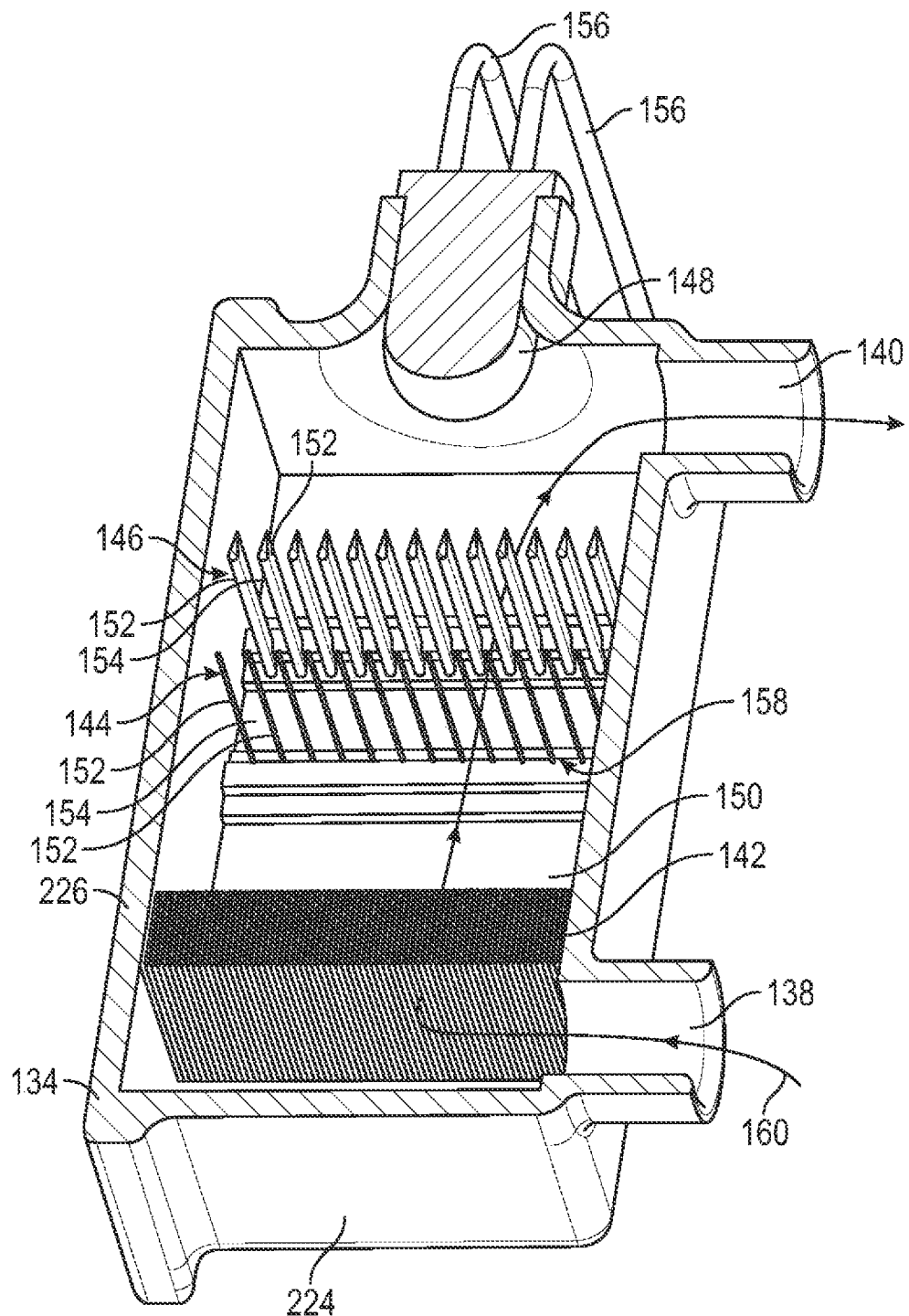
FIG. 10 is a top cross-sectional view of the ozone generating chamber shown in FIG. 9, taken along line B-B' in FIG. 9.

As can be seen in FIG. 3, the ozone generation assembly 16 includes an ozone generating chamber 134, a controller 136 with a built-in battery, and wires 156 that run between the ozone generating chamber 134 and the controller 136. The ozone generating chamber 134 is shown in FIGS. 9 to 11 as having an exterior wall 224 that defines an internal compartment 150. In FIG. 9, a rear panel 226 of the exterior wall 224 is removed to show that the internal compartment 150 contains a desiccant 142, a first electrode 144, a second electrode 146, and a sensor 148. The ozone generating chamber 134 has two openings, referred to herein as the air inlet 138 and the air outlet 140, that are in fluid communication with the internal compartment 150. The internal compartment 150 is sealed other than at the air inlet 138 and the air outlet 140.

As can be seen in FIGS. 4 and 11, the air inlet 138 is a cylindrical tube that receives the air outlet tube 34 extending rearwardly from the piston chamber forming element 24, and the air outlet 140 is a cylindrical tube that receives the air inlet tube 32 extending rearwardly from the piston chamber forming element 24. The air inlet 138 of the ozone generating chamber 134 is thus in fluid communication with the air compartment 110 via the air outlet tube 34, and the air outlet 140 of the ozone generating chamber 134 is in fluid communication with the air compartment 110 via the air inlet tube 32, as shown in FIG. 11.

The desiccant 142 is positioned within the internal compartment 150 adjacent to the air inlet 138, and extends across the ozone generating chamber 134 such that any air that passes through the internal compartment 150 from the air inlet 138 to the air outlet 140 must pass through the desiccant 142. The desiccant 142 is made from a suitable material that removes moisture from the air, as is known in the art.

The first electrode 144 is positioned within the internal compartment 150 between the desiccant 142 and the air outlet 140, and comprises a plurality of elongated electrode members 152 that extend vertically from the bottom of the ozone generating chamber 134 to the top of the ozone generating chamber 134, as can be seen in FIG. 10. Each electrode member 152 of the first electrode 144 is a thin rod made from a suitably conductive material. The electrode members 152 are arranged in a line extending from the back of the ozone generating chamber 134 to the front of the ozone generating chamber 134, with each electrode member 152 being horizontally spaced from the adjacent electrode members 152 so that air flow passages 154 are defined between the electrode members 152. The first electrode 144 optionally functions as a positively charged anode.

The second electrode 146 is positioned within the internal compartment 150 between the first electrode 144 and the air outlet 140. The second electrode 146 also comprises a plurality of elongated electrode members 152 that extend vertically from the bottom of the ozone generating chamber 134 to the top of the ozone generating chamber 134. Each electrode member 152 of the second electrode 146 has a tear drop shape in horizontal cross-section, with a rounded end facing towards the first electrode 144 and a pointed end facing away from the first electrode 144. The electrode members 152 of the second electrode 146 are made from a suitably conductive material, and are arranged in a line extending from the back of the ozone generating chamber 134 to the front of the ozone generating chamber 134, with each electrode member 152 being horizontally spaced from the adjacent electrode members 152 so that air flow passages 154 are defined between the electrode members 152. The second electrode 146 optionally functions as a negatively charged cathode.

The first electrode 144 and the second electrode 146 are each attached to one of the wires 156, as best shown in FIG. 9. The wires 156 electrically connect the first electrode 144 and the second electrode 146 to the controller 136, which is configured to generate a sufficiently high voltage between the first electrode 144 and the second electrode 146 to generate a corona discharge. The first electrode 144 and the second electrode 146 thus function as a corona discharge generator 158. As is known, corona discharges can be used to generate ozone from the oxygen in air.

The sensor 148 is positioned near the air outlet 140 facing towards the second electrode 146, and is attached to the controller 136 by wires 156. The sensor 148 is configured to sense a concentration of ozone in the ozone generating chamber 134, or sense a parameter that can be used for estimating or calculating the concentration of ozone in the ozone generating chamber 134.

An exemplary method of operating the foam dispenser 10 will now be described with reference to FIGS. 3 to 11. The foam dispenser 10 shown in FIG. 3 is preferably mounted to a dispenser housing, not shown, so that the piston forming body 22 is axially movable relative to the piston chamber forming element 24 between the extended position shown in FIG. 5 and the retracted position shown in FIG. 7 upon activation of a pump actuator of the dispenser housing. Between activations, the piston forming body 22 is preferably held in the extended position shown in FIG. 5. When in the extended position, the air compartment 110 is filled with air, and the liquid compartment 84 is filled with the foamable liquid.

To activate the corona discharge generator 158, the controller 136 applies a sufficiently high voltage between the first electrode 144 and the second electrode 146 to produce a corona discharge, which generates ozone from the oxygen in the surrounding air. The corona discharge also produces ions in the air adjacent to the first electrode 144, which are attracted to the second electrode 146. The ions may, for example, include nitrogen ions. As the ions move from the first electrode 144 towards the second electrode 146 they collide with air molecules, which produces a flow of air molecules from the first electrode 144 towards the second electrode 146. When the air molecules reach the second electrode 146 they pass through the air passages 154 between the electrode members 152, and then continue flowing out of the ozone generating chamber 134 through the air outlet 140 and the air inlet tube 32 into the air compartment 110. This flow of air generated by the corona discharge is referred to herein as an ionic wind. The corona discharge generator 158 thus functions as an air flow generator 178, in addition to an ozone generator 176.

The ionic wind circulates air between the air compartment 110 and the ozone generating chamber 134 in an air flow path 160 as shown in FIG. 11. In the air flow path 160, the air inlet 138 is upstream from the desiccant 142, the desiccant 142 is upstream from the first electrode 144, the first electrode 144 is upstream from the second electrode 146, and the second electrode 146 is upstream from the air outlet 140.

When the ionic wind moves air away from the first electrode 144 towards the second electrode 146 as described above, this generates a vacuum pressure in the vicinity of the first electrode 144, which draws air along the air flow path 160 from the air compartment 110 into the internal compartment 150 of the ozone generating chamber 134 through the air outlet tube 34 and the air inlet 138, and then through the desiccant 142 towards the first electrode 144. The air passages 154 between the electrode members 152 of the first electrode 144 allow the air to flow past the first electrode 144, where it is further accelerated towards the second electrode 146 by the ions generated by the corona discharge. The tear drop shape of the electrode members 152 of the second electrode 146 provides a smooth and aerodynamic pathway for the air, including the ozone generated by the corona discharge, to continue flowing past the electrode members 152 of the second electrode 146 through the air passages 154. The movement of the air past the second electrode 146 produces a zone of relatively high air pressure adjacent to the air outlet 140, which causes the ozonated air to flow out of the internal compartment 150 of the ozone generating chamber 134 back into the air compartment 110 through the air outlet 140 and the air inlet tube 32. The ozonated air expelled from the air outlet 140 into the air compartment 110 travels in a curved circulation path that encircles the outer surface 102 of the inner wall 38. This provides for thorough mixing of the ozonated air, so that preferably the concentration of ozone is substantially uniform throughout the air compartment 110.

Figure 6:
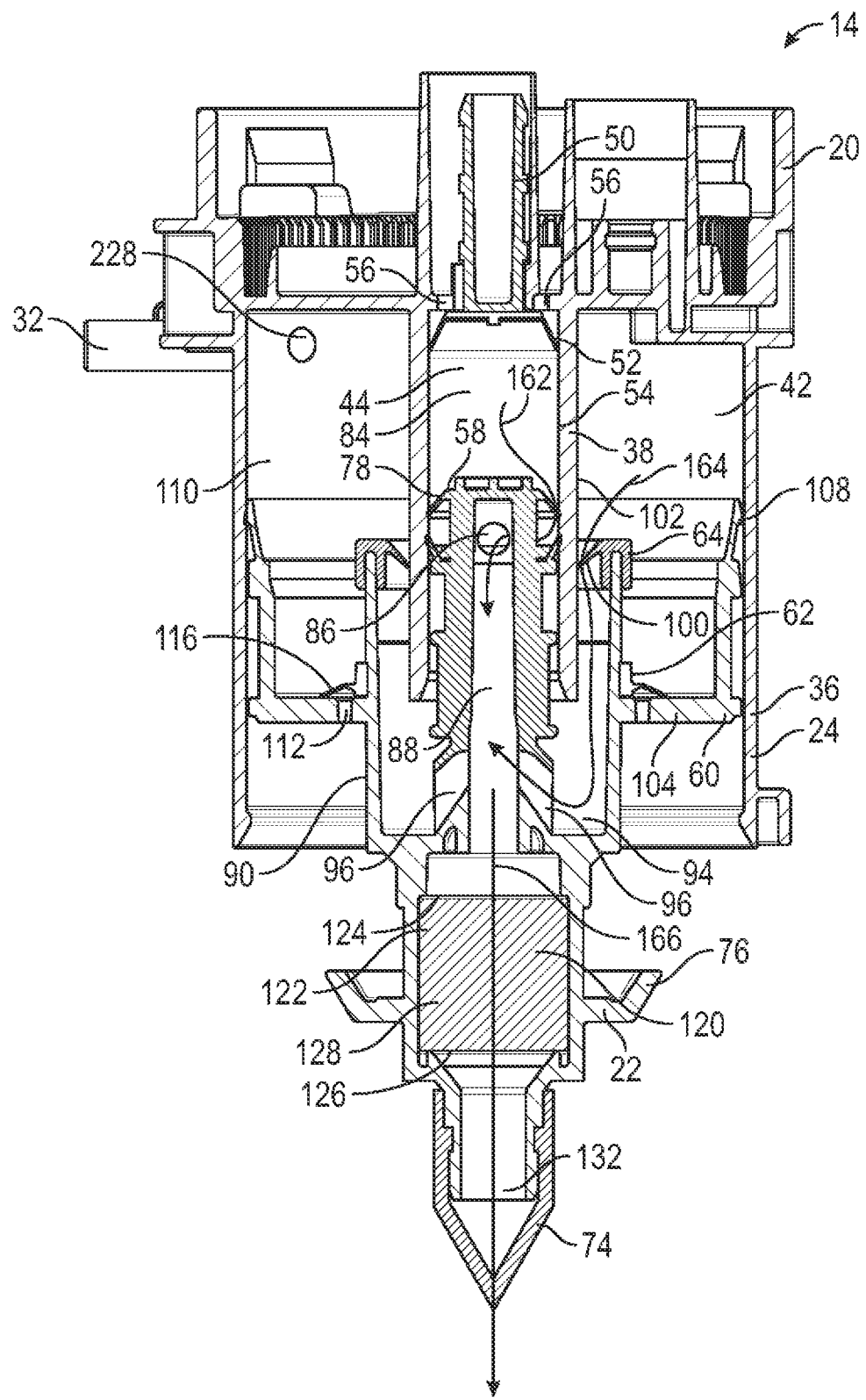
FIG. 6 is a left side cross-sectional view of the piston pump shown in FIG. 4, taken alone line A-A' in FIG. 4, and showing the piston pump in an intermediate position during a retraction stroke.
Figure 7:
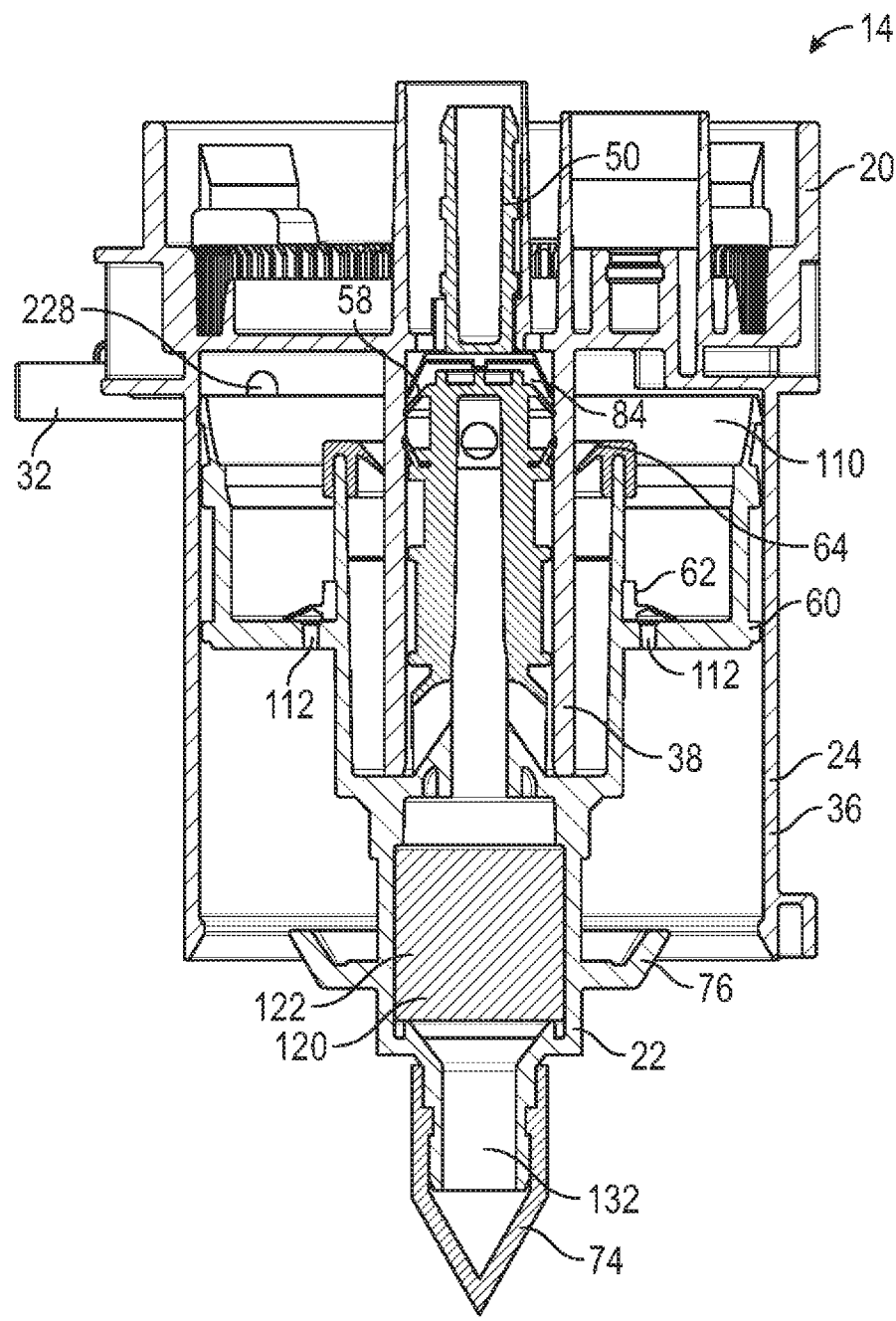
FIG. 7 is a left side cross-sectional view of the piston pump shown in FIG. 4, taken alone line A-A' in FIG. 4, and showing the piston pump in a retracted position.
Figure 8:
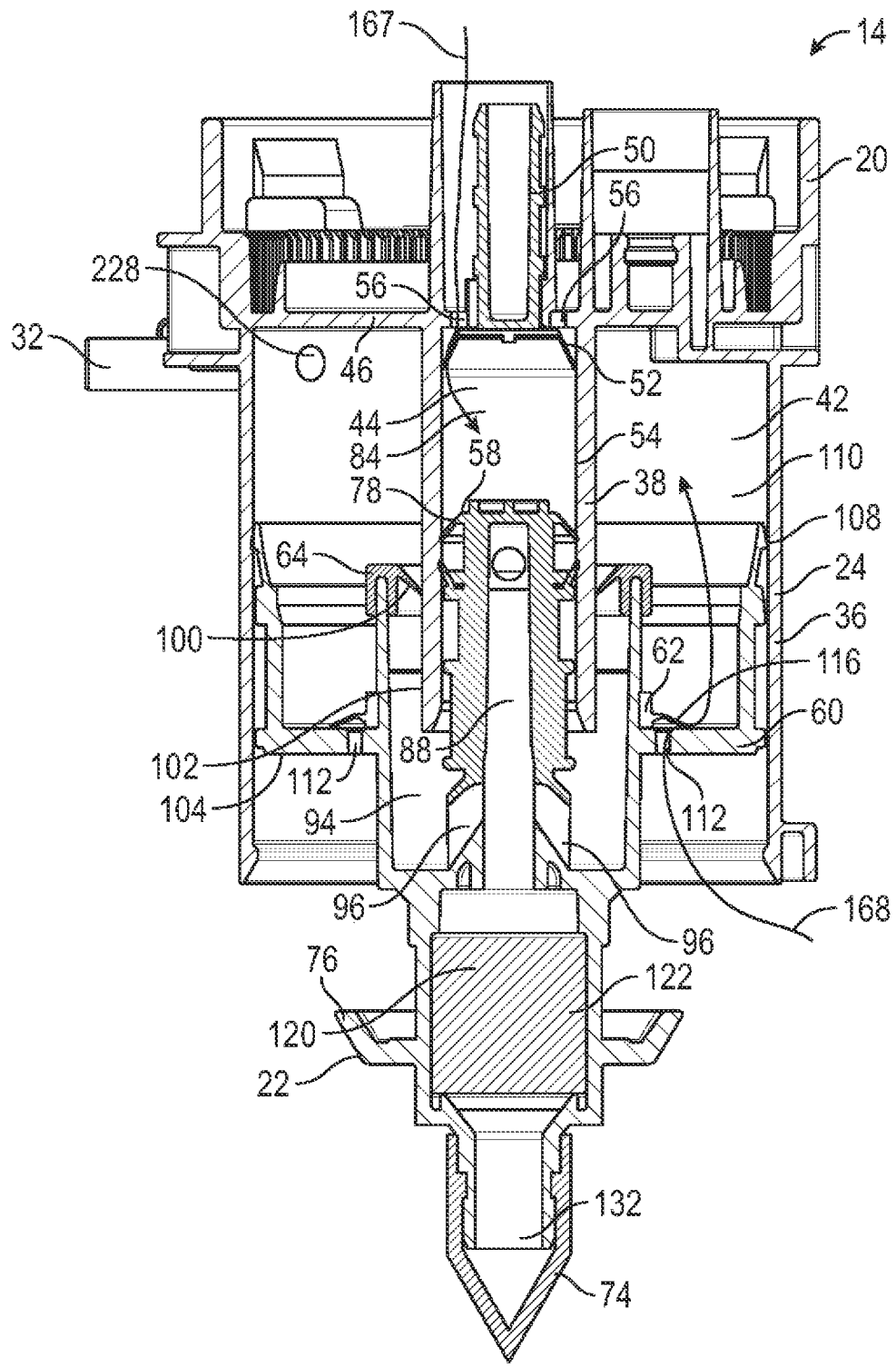
FIG. 8 is a left side cross-sectional view of the piston pump shown in FIG. 4, taken alone line A-A' in FIG. 4, and showing the piston pump in the intermediate position during an extension stroke.

When the dispenser 10 is activated, the piston forming body 22 moves axially inwardly relative to the piston chamber forming element 24 in a dispensing stroke from the extended position shown in FIG. 5, past the intermediate position shown in FIG. 6, to the retracted position shown in FIG. 7. The movement of the liquid displacement portion 58 axially inwardly into the liquid chamber 44 during the dispensing stroke decreases the volume of the liquid compartment 84. This causes the pressure of the foamable liquid within the liquid compartment 84 to increase, which deforms the disc member 78 of the liquid displacement portion 58 axially outwardly and radially inwardly, out of engagement with the inner surface 54 of the inner wall 38. This allows the foamable liquid to flow past the disc member 78, through the liquid receiving opening 86, and into the inner liquid channel 88, as shown by the arrow 162 in FIG. 6. The engagement of the deformable disc 52 of the one-way liquid inlet valve 50 with the inner surface 54 of the inner wall 38 prevents the foamable liquid from flowing out of the liquid compartment 84 into the reservoir 12.

The simultaneous movement of the air displacement portion 60 axially inwardly into the air chamber 42 during the dispensing stroke decreases the volume of the air compartment 110. This causes the air pressure within the air compartment 110 to increase, which deforms the inner rim 100 of the one-way air outlet valve 64 axially outwardly and radially outwardly, out of engagement with the outer surface 102 of the inner wall 38. This allows the ozonated air to flow past the one-way air outlet valve 64, through the outer air channel 94, and into the inner liquid channel 88 via the air introduction channels 96, as shown by the arrow 164 in FIG. 6. The engagement of the ring-shaped flange 116 of the one-way air inlet valve 62 with the radial extension wall 104 prevents the ozonated air from being expelled from the air compartment 110 through the air inlet openings 112.

The ozonated air and the foamable liquid then pass axially outwardly through the foam generator 122, where they are thoroughly mixed together to generate an ozone containing foam. The foam is then discharged from the dispenser 10 through the discharge outlet 132 and the one-way foam outlet valve 74. The piston forming body 22 and the piston chamber forming element 24 thus function as a liquid pump 172 that delivers the foamable liquid from the reservoir 12 to the foam generator 122, and as an air pump 174 that simultaneously delivers the ozonated air from the air compartment 110 to the foam generator 122. The path of the ozonated air and the foamable liquid through the foam generator 122 and out of the discharge outlet 132 as foam is shown by the arrow 166 in FIG. 6. The discharged ozone containing foam can be used to, for example, sanitize a user's hands.

At the end of the dispensing stroke, the piston forming body 22 is located at the retracted position shown in FIG. 7. The piston forming body 22 then begins moving axially outwardly relative to the piston chamber forming element 24 in a recharging stroke from the retracted position shown in FIG. 7, past the intermediate position shown in FIG. 8, to the extended position shown in FIG. 5. The movement of the liquid displacement portion 58 axially outwardly within the liquid chamber 44 during the recharging stroke increases the volume of the liquid compartment 84. This causes the pressure of the foamable liquid within the liquid compartment 84 to decrease, which deforms the deformable disc 52 of the one-way liquid inlet valve 50 axially outwardly and radially inwardly, out of engagement with the inner surface 54 of the inner wall 38. This allows the foamable liquid contained within the fluid reservoir 12 to flow through the liquid inlet openings 56, past the one-way liquid inlet valve 50, and into the liquid compartment 84, as shown by the arrow 167 in FIG. 8. The engagement of the disc member 78 of the liquid displacement portion 58 with the inner surface 54 of the inner wall 38 prevents any fluid remaining within the inner liquid channel 88 from being drawn back into the liquid compartment 84.

The simultaneous movement of the air displacement portion 60 axially outwardly within the air chamber 42 during the recharging stroke increases the volume of the air compartment 110. This causes the air pressure within the air compartment 110 to decrease, which deforms the ring-shaped flange 116 of the one-way air inlet valve 62 axially inwardly, out of engagement with the radial extension wall 104. This allows atmospheric air to flow through the air inlet openings 112, past the one-way air inlet valve 62, and into the air compartment 110, as shown by the arrow 168 in FIG. 8. The engagement of the inner rim 100 of the one-way air outlet valve 64 with the outer surface 102 of the inner wall 38 prevents any fluid remaining within the outer air channel 94 from being drawn back into the air compartment 110, thereby preventing the foamable liquid from entering the air compartment 110 and rapidly saturating the desiccant 142.

At the end of the recharging stroke, the piston forming body 22 is located back at the extended position shown in FIG. 5, with the liquid compartment 84 filled with foamable liquid ready to be dispensed, and with the air compartment 110 filled with air.

Optionally, the controller 136 is configured to activate the corona discharge generator 158 to generate ozone when the piston forming body 22 is in the extended position. The controller 136 is configured to activate the corona discharge generator 158 for a sufficient length of time so that the concentration of ozone within the air compartment 110 falls within a preselected range of acceptable concentrations. The range of concentrations that is considered acceptable will depend on the intended use of the foam, and the invention is not limited to any particular range of concentrations. Preferably, the controller 136 is able to calculate or estimate the concentration of ozone in the air compartment 110 based on data received from the sensor 148, and adjusts the duration and/or intensity of the corona discharge as needed so that the concentration falls within the preselected range. Alternatively, the sensor 148 could be omitted and the controller 136 could be configured to activate the corona discharge generator 158 for a set length of time and at an intensity that is known to generate an acceptable concentration of ozone. Optionally, the controller 136 is configured to determine or estimate the concentration of ozone within the air compartment 110 over time, based on periodic measurements by the sensor 148 and/or based on a known rate of ozone decomposition. The controller 136 preferably maintains the concentration of ozone within the air compartment 110 within the preselected range of acceptable concentrations at all times, by periodically activating the corona discharge generator 158 when necessary. This ensures that there is always a supply of ozone ready to be dispensed immediately when needed. Alternatively, the controller 136 could be configured to activate the corona discharge generator 158 only after the dispenser 10 has been activated, with the result that there may be a brief delay while the ozone is being generated before it can be dispensed.

Optionally, after each activation of the dispenser 10 the return of the piston forming body 22 to the extended position triggers the controller 136 to activate the corona discharge generator 158 to provide the air compartment 110 with the preselected concentration of ozone. More preferably, the corona discharge generator 158 is activated during the recharging stroke. This allows the ozone to immediately begin accumulating within the air compartment 110, so that the air compartment 110 preferably already contains the preselected concentration of ozone when the piston forming body 22 reaches the extended position. If the air compartment 110 already contains the preselected concentration of ozone when the piston forming body 22 reaches the extended position, then no delay is required before a subsequent allotment of ozone containing foam can be dispensed from the dispenser 10. Alternatively, if the air compartment 110 does not contain the preselected concentration of ozone when the piston forming body 22 reaches the extended position, then a short delay may be required to generate the preselected concentration of ozone before a subsequent allotment of ozone containing foam can be dispensed from the dispenser 10.

The piston pump 14 and the reservoir 12 are preferably removable from a housing of the dispenser 10 so that they can be replaced when the foamable liquid within the reservoir 12 is depleted. The reservoir 12 and the piston pump 14 may, for example, be removable from the housing by sliding the reservoir 12 and the piston pump 14 forwardly out of engagement with the housing. Optionally, the ozone generation assembly 16 detaches from the piston pump 14 and remains attached to the housing when the reservoir 12 and the piston pump 14 are removed. The ozone generation assembly 16 can be detached from the piston pump 14 by sliding the piston pump forwardly, away from the ozone generation assembly 16, so that the air inlet tube 32 and the air outlet tube 32 of the piston pump 14 slide out of engagement with the air inlet 138 and the air outlet 140 of the ozone generating chamber 134. Once the piston pump 14 and the reservoir 12 are removed, a replacement piston pump 14 and a replacement reservoir 12 with a new supply of the foamable liquid can be installed by sliding the piston pump 14 and reservoir 12 rearwardly into the housing, with the air inlet tube 32 and the air outlet tube 32 of the replacement piston pump 14 sliding into engagement with the air inlet 138 and the air outlet 140 of the ozone generating chamber 134. This allows the ozone generation assembly 16 to be reused over time, while also allowing the reservoir 12 and the piston pump 14 to be periodically replaced when needed. A suitable arrangement for providing an ozone generator 176 that is removably attached to a piston pump 14 is disclosed in U.S. Pat. No. 8,733,596, which is incorporated herein by reference.

The foam dispenser 10 as shown in FIGS. 3 to 11 is broadly similar to the ozone generation and storage device 200 as shown in FIG. 1. In particular, as best shown in FIG. 11, the air compartment 110 of FIG. 11 broadly corresponds to the storage compartment 202 of FIG. 1; the ozone generating chamber 134 of FIG. 11 broadly corresponds to the ozone generation compartment 204 of FIG. 1; and the air inlet tube 32 and air outlet tube 34 received by the air inlet 138 and air outlet 140 of FIG. 11 broadly correspond to the fluid circulation tubes 206, 208 of FIG. 1. Similarly to the embodiment shown in FIG. 1, in the embodiment of FIG. 11 the ionic wind circulates the ozonated air in a circular air flow path 160 through an internal ozone circulation compartment 214 that is defined by the air compartment 110, the ozone generating chamber 134, the air inlet tube 32, the air outlet tube 34, the air inlet 138, and the air outlet 140. The piston pump 14 of FIG. 11 also broadly corresponds to the fluid pump 216 of FIG. 1.

Figure 12:
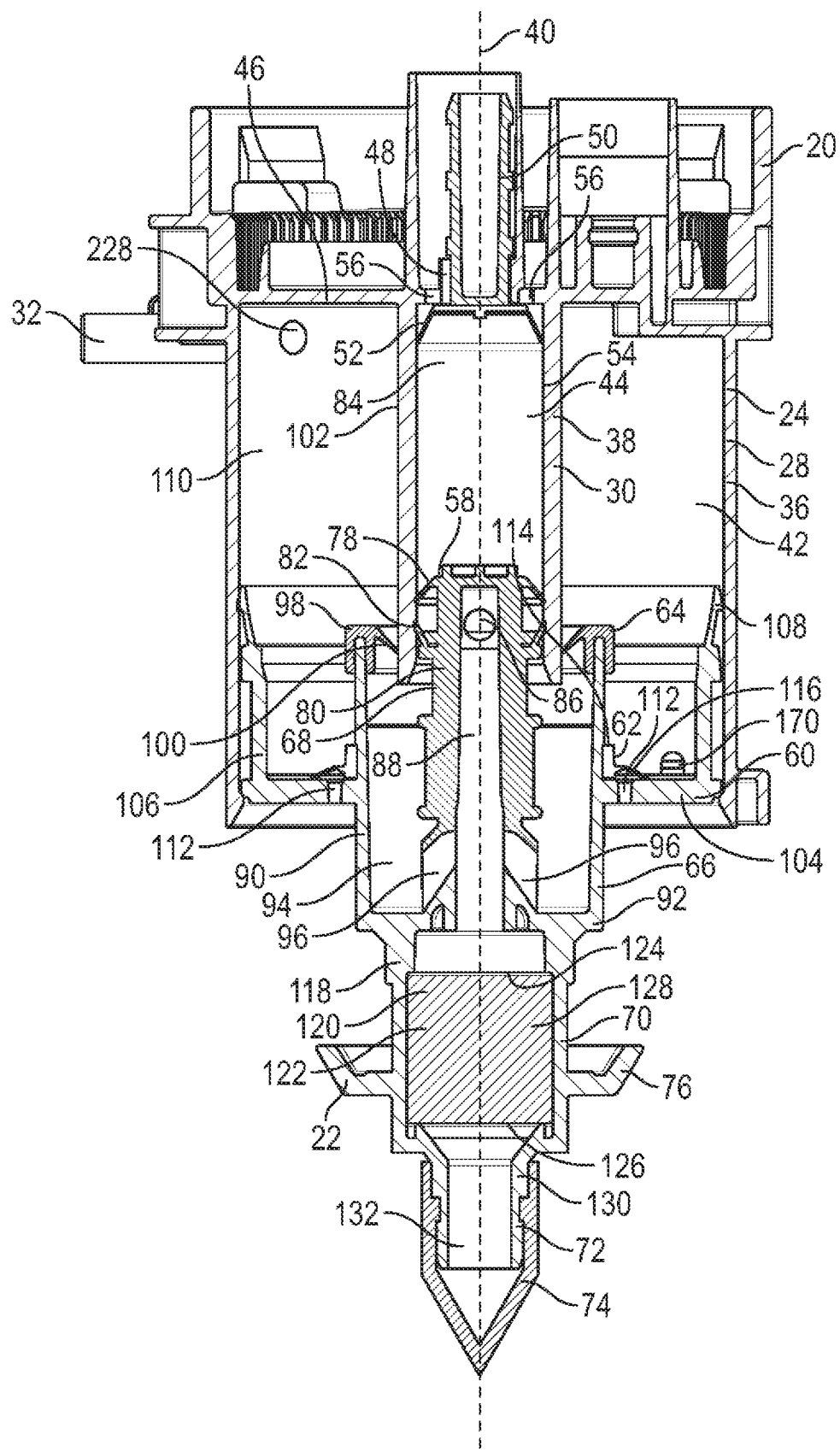
FIG. 12 is a left side cross-sectional view of a piston pump of a foam dispenser in accordance with a fourth embodiment of the present invention.

Reference is now made to FIG. 12, which shows a piston pump 14 of a foam dispenser 10 in accordance with a fourth preferred embodiment of the invention. The piston pump 14 shown in FIG. 12 is identical to the pump 14 shown in FIGS. 3 to 11, with the only difference being that an ozone sensor 170 is positioned within the air compartment 110. Like numerals are used to denote like components.

As can be seen in FIG. 12, the ozone sensor 170 is attached to the air displacement portion 60 of the piston forming body 22. The ozone sensor 170 directly measures the concentration of ozone within the air compartment 110, and preferably transmits the measurement data through a wired or wireless connection to the controller 136. The measurement data is preferably used by the controller 136 to determine whether the concentration of ozone within the air compartment 110 falls within the preselected range of acceptable concentrations, so that the controller 136 can activate or deactivate the corona discharge generator 158 as necessary.

The piston pump 14 shown in FIG. 12 can be operated in exactly the same manner as in the embodiment shown in FIGS. 3 to 11, except with the ozone sensor 170 preferably providing the controller 136 with additional information about the concentration of ozone within the air compartment 110. The ozone sensor 170 could be placed at any desired location, and is not limited to being attached to the piston forming body 22. The ozone sensor 170 could, for example, be attached to the partition wall 46 and extend downwardly into the air compartment 110. If the ozone sensor 170 is attached to the partition wall 46, the ozone sensor 170 will remain stationary during operation of the piston pump 14. This may be advantageous if, for example, the ozone sensor 170 is wired to a stationary power source.

Figure 13:
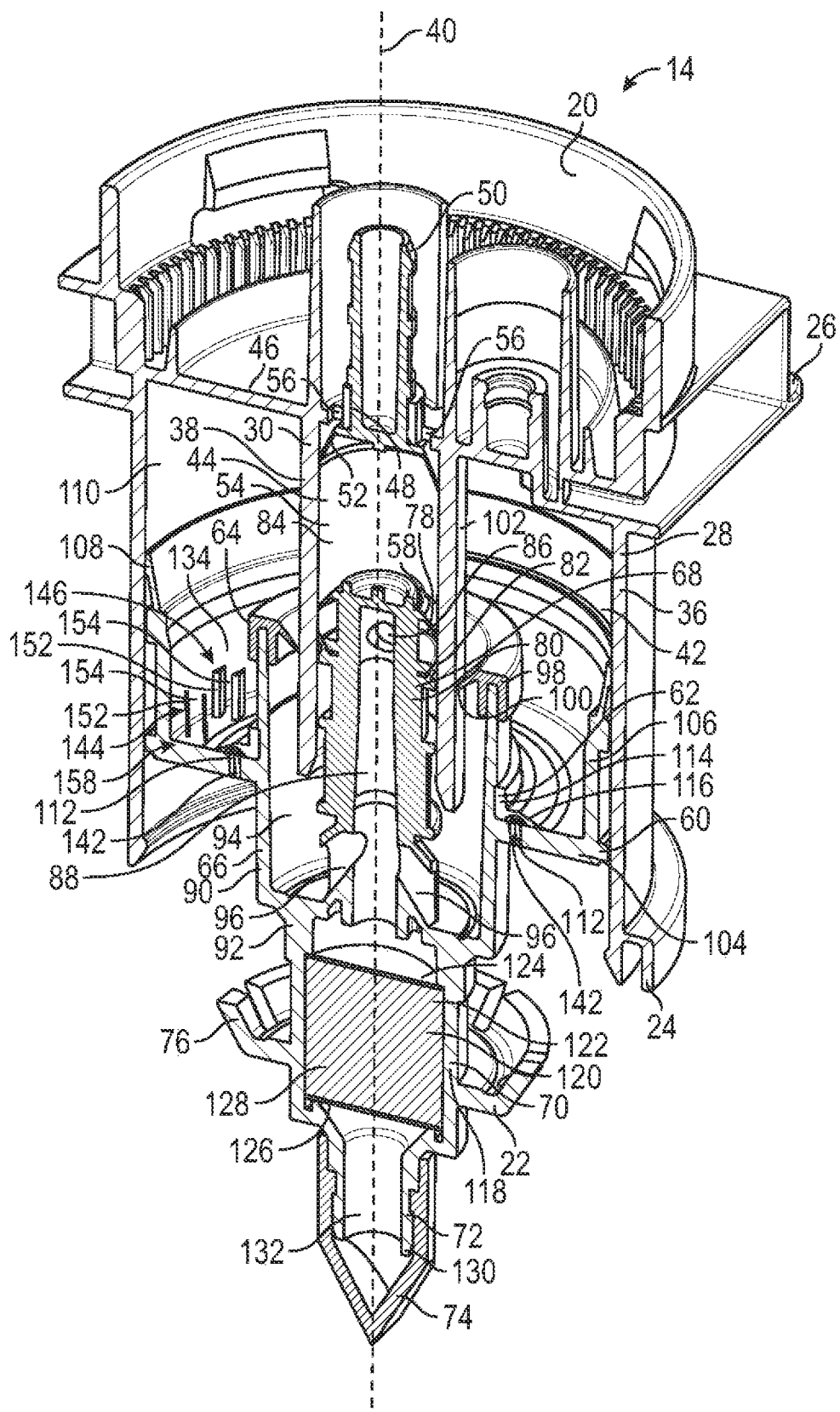
FIG. 13 is a perspective left side cross-sectional view of a piston pump of a foam dispenser in accordance with a fifth embodiment of the present invention.

Reference is now made to FIG. 13, which shows a piston pump 14 of a foam dispenser 10 in accordance with a fifth preferred embodiment of the invention. The piston pump 14 shown in FIG. 12 is identical to the pump 14 shown in FIGS. 3 to 11, with the notable difference that the air compartment 110 has been adapted to function as the ozone generating chamber 134. The specific structural changes that allow the air compartment 110 to function as the ozone generating chamber 134 are described in more detail below. Like numerals are used to denote like components.

As can be seen in FIG. 13, the first electrode 144 and the second electrode 146 extend axially inwardly into the air compartment 110 from the radial extension wall 104 of the piston forming body 22, rather than being located in a separate chamber, and each of the air inlet openings 112 contain a desiccant 142. The desiccant 142 helps to remove moisture from the atmospheric air that is drawn into the air compartment 110 through the air inlet openings 112. Unlike the embodiment shown in FIGS. 3 to 11, in the embodiment shown in FIG. 13 there is no air inlet tube 32 or air outlet tube 34.

The piston pump 14 shown in FIG. 13 can be operated in substantially the same manner as the embodiment shown in FIGS. 3 to 11, but with the ozone being generated directly within the air compartment 110 rather than in a separate chamber. To generate ozone, the controller 136, which is not shown in FIG. 13, applies a sufficiently high voltage between the first electrode 144 and the second electrode 146 to generate a corona discharge. The corona discharge generates ozone from the oxygen in the air contained within the air compartment 110, and also generates an ionic wind. The ionic wind propels the ozonated air away from the corona discharge generator 158, so that the ozonated air is thoroughly circulated and mixed throughout the entire air compartment 110. As a result, the concentration of ozone within the air compartment 110 is preferably substantially uniform.

Once the concentration of ozone within the air compartment 110 is within a preselected range of concentrations, as measured and/or calculated and/or estimated, then the piston forming body 22 can be moved axially inwardly relative to the piston chamber forming element 24 in a dispensing stroke to dispense an allotment of the ozone containing foam, and then axially outwardly relative to the piston chamber forming element 24 in a recharging stroke to fill the liquid compartment 84 with the foamable liquid and to fill the air compartment 110 with atmospheric air. The dispensing stroke and the recharging stroke of the pump 14 shown in FIG. 13 are identical to the dispensing stroke and the recharging stroke of the pump 14 shown in FIGS. 3 to 11, with the only difference being that the atmospheric air that is drawn in through each of the air inlet openings 112 during the recharging stroke passes through the desiccant 142, which helps to remove the moisture from the atmospheric air.

The first electrode 144 and the second electrode 146 could be placed at any desired location, and are not limited to being attached to the piston forming body 22 as shown in FIG. 13. The first electrode 144 and the second electrode 146 could, for example, be attached to the partition wall 46 and extend downwardly into the air compartment 110. If the first electrode 144 and the second electrode 146 are attached to the partition wall 46, the first electrode 144 and the second electrode 146 will remain stationary during operation of the piston pump 14. This may be advantageous if, for example, the first electrode 144 and the second electrode 146 are wired to a stationary controller 136.

The embodiments shown in FIGS. 3 to 12 therefore provide a dispenser 10 for dispensing ozone containing foam, the dispenser 10 comprising: an ozone generating chamber 134 having an air inlet 138 in communication with a source of air and an air outlet 140, the ozone generating chamber 134 containing a corona discharge generator 158 that generates a corona discharge to produce: (a) ozonated air, by converting oxygen in the air into ozone, and (b) an ionic wind that draws the air from the air source into the ozone generating chamber 134 through the air inlet 138, and expels the ozonated air from the ozone generating chamber 134 through the air outlet 140; a foam generator 122 that receives the ozonated air expelled from the ozone generating chamber 134 and mixes the ozonated air with a foamable liquid to generate the ozone containing foam; and a discharge outlet 132 for discharging the ozone containing foam.

The embodiments shown in FIGS. 3 to 12 also provide a dispenser 10 for dispensing ozone containing foam, the dispenser 10 comprising: an ozone generating chamber 134 having an air inlet 138 and an air outlet 140, the ozone generating chamber 134 having an ozone generator 176 that generates ozonated air inside the ozone generating chamber 134 by converting oxygen in air into ozone; an air compartment 110 that contains a supply of air and is in fluid communication with the air inlet 138 and the air outlet 140; an air flow generator 178 that circulates air and ozonated air between the air compartment 110 and the ozone generating chamber 134 in an air flow path 160 from the air compartment 110 into the ozone generating chamber 134 through the air inlet 138, and from the ozone generating chamber 134 into the air compartment 110 through the air outlet 140; a foam generator 122 that receives the ozonated air from the air compartment 110 and mixes the ozonated air with a foamable liquid to generate the ozone containing foam; and a discharge outlet 132 for discharging the ozone containing foam.

The embodiments shown in FIGS. 3 to 13 furthermore provide a dispenser 10 for dispensing ozone containing foam, the dispenser 10 comprising: an ozone generating chamber 134 having a corona discharge generator 158 that generates a corona discharge to produce: (a) ozonated air, by converting oxygen in air into ozone, and (b) an ionic wind that circulates the ozonated air; a foam generator 122 that receives the ozonated air and mixes the ozonated air with a foamable liquid to generate the ozone containing foam; and a discharge outlet 132 for discharging the ozone containing foam; wherein the corona discharge generator 158 comprises a first electrode 144 and a second electrode 146; wherein the first electrode 144 produces ions that are attracted to the second electrode 146; and wherein the ionic wind is generated by movement of the ions from the first electrode 144 towards the second electrode 146.

It will be understood that, although various features of the invention have been described with respect to one or another of the embodiments of the invention, the various features and embodiments of the invention may be combined or used in conjunction with other features and embodiments of the invention as described and illustrated herein.

The present invention is not limited to the particular construction of the foam dispenser 10 as shown and described herein. For example, the piston pump 14 could optionally be provided with a stepped construction as shown in U.S. Pat. No. 7,267,251 to Ophardt, issued Dec. 11, 2007, or U.S. Pat. No. 8,272,539 to Ophardt et al., issued Sep. 25, 2012, which are incorporated herein by reference. With a stepped construction, the air chamber 42 and the liquid chamber 44 can be configured so that the volume of the air compartment 110 and the liquid compartment 84 increases during the retraction stroke and decreases during the extension stroke, so that the ozone containing foam is dispensed during the extension stroke rather than the retraction stroke, and the air compartment 110 and the liquid compartment 84 are refilled during the retraction stroke rather than the extension stroke. Any other type of fluid pump 216, air pump 174, and/or liquid pump 172 could also be used, and the invention is not limited to embodiments that use a piston pump 14. The invention could, for example, use one or more of the fluid pumps 216, air pumps 174, and liquid pumps 172 disclosed in U.S. Patent Application Publication No. 2014/0099224 to Ophardt et al., published Apr. 10, 2014; U.S. Patent Application Publication No. 2018/0344101 to Jones et al., published Dec. 6, 2018; U.S. Patent Application Publication No. 2015/0291345 to Ophardt et al., published Oct. 15, 2015; U.S. Patent Application Publication No. 2017/0055782 to Ophardt et al., published Mar. 2, 2017; U.S. Patent Application Publication No. 2018/0304284 to Ophardt et al., published Oct. 25, 2018; or U.S. Patent Application Publication No. 2019/0054485 to Ophardt et al., published Feb. 21, 2019, which are incorporated herein by reference.

The structure of the ozone generating chamber 134 may also differ from the structure shown and described herein. For example, the ozone generating chamber 134 could optionally have a curved or rounded construction that assists in directing the circulating air from the air inlet 138 to the air outlet 140. Although the air inlet 138 and the air outlet 140 are shown in the preferred embodiments as both being in fluid communication with the air compartment 110, this is not necessary. For example, the air inlet 138 could be in fluid communication with a separate air source, such as the atmosphere. When the air inlet 138 is in fluid communication with an air source other than the air compartment 110, the corona discharge generator 158 is preferably configured to generate a corona discharge during the recharging stroke of the piston pump 14, so that the volume of the air compartment 110 is increasing to accommodate the ozonated air that is directed into the air compartment 110 by the ionic wind. Optionally, when the air inlet 138 is in fluid communication with an air source other than the air compartment 110, the air inlet openings 112 in the radial extension wall 104 can be omitted, so that all of the air received by the air compartment 110 comes from the ozone generating chamber 134. The air inlet 138 could also be provided with a one-way valve that allows the atmospheric air to enter the ozone generating chamber 134 through the air inlet 138, and prevents the ozonated air from exiting the ozone generating chamber 134 through the air inlet 138.

The corona discharge generator 158 could also have a different structure from the structure shown and described herein. For example, the corona discharge generator 158 could optionally have a structure similar to that shown and described in U.S. Pat. No. 3,638,058 to Fritzius, issued Jan. 25, 1972, which is incorporated herein by reference. Preferably, the first electrode 144 and the second electrode 146 have a structure that provides air passages 154 through or adjacent to the first electrode 144 and the second electrode 146 that allow air to flow past the first electrode 144 and the second electrode 146 to generate the ionic wind.

Figure 14:
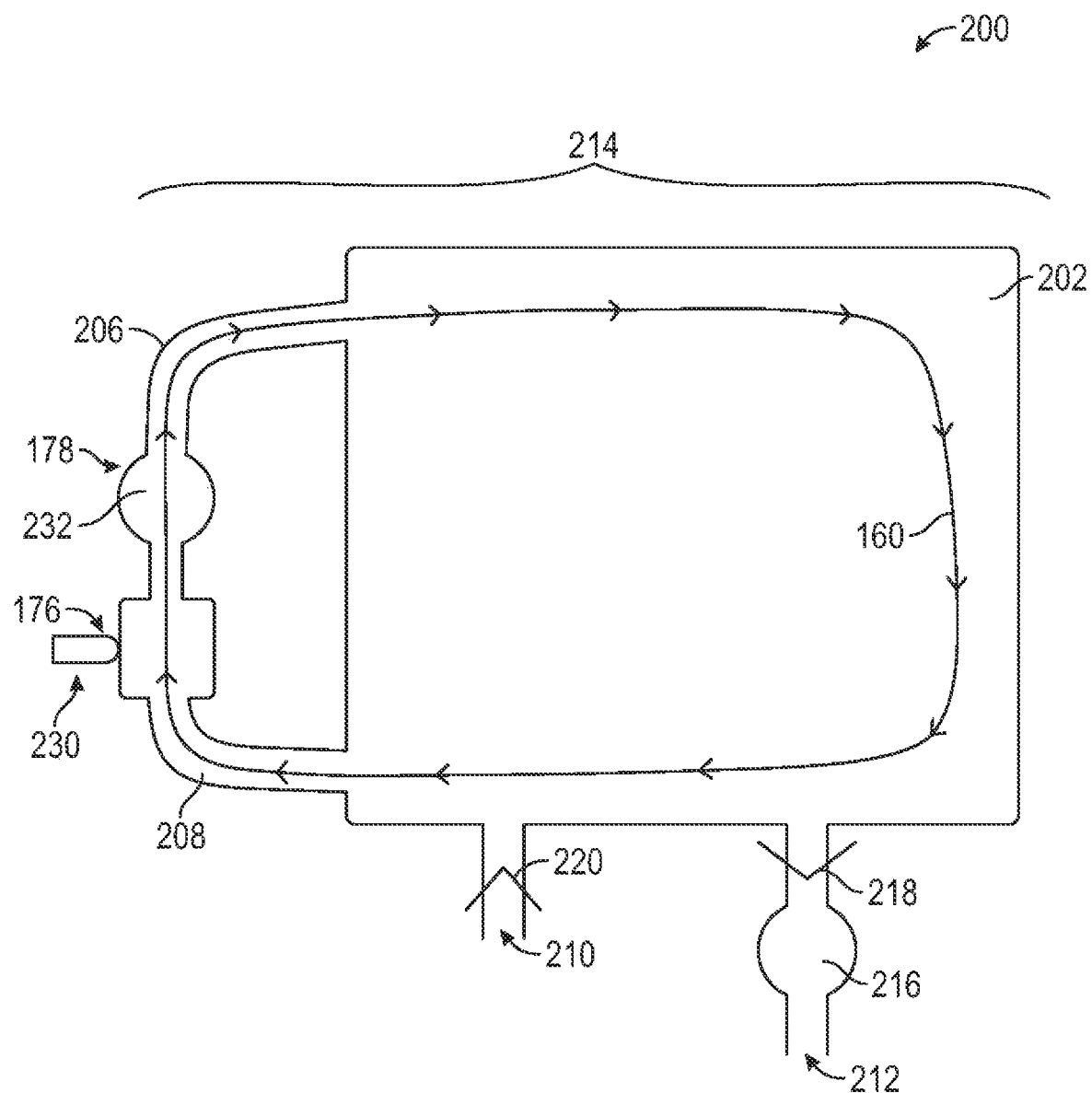
FIG. 14 is a schematic representation of an ozone generation and storage device in accordance with a sixth embodiment of the present invention.

Alternatively, in some configurations of the invention the corona discharge generator 158 could be omitted entirely, and another type of ozone generator 176 could be used instead. For example, as shown schematically in FIG. 14, wherein like numerals denote like components, a UV radiation ozone generator 230 could be used to generate the ozone. However, when the corona discharge generator 158 is omitted as in FIG. 14, there is no ionic wind, and so an alternative mechanism for circulating the ozone is required. For example, as shown schematically in FIG. 14, a conventional air fan 232 could be used as the air flow generator 178. Because corona discharge generators 158 are able to serve as both an ozone generator 176 and an air flow generator 178, it is preferred, though not strictly necessary, to use a corona discharge generator 158 rather than an alternative type of ozone generator 176.

In some embodiments of the invention, such as the embodiment shown in FIG. 13, the corona discharge generator 158 is located within the air compartment 110, rather than in a separate ozone generating chamber 134. In this case, the air chamber 42 can be thought of as also serving as the ozone generating chamber 134, with the result that the ozone generating chamber 134 defines, or at least partially defines, the air compartment 110. When the corona discharge generator 158 is located within the air compartment 110, the corona discharge generator 158 generates the ozonated air directly within the air compartment 110, and the ionic wind circulates the ozonated air throughout the air compartment 110. Preferably, the air compartment 110 has a generally cylindrical shape, with for example the liquid chamber 44 extending axially through the center of the air compartment 110, so that the ozonated air is directed in a curved circulation path that encircles the liquid chamber 44, and evenly distributes the ozonated air throughout the air compartment 110. However, any other suitable shape of the air compartment 110 that allows for the thorough mixing and circulation of the ozonated air could be used instead.

The invention is not limited to the particular method of generating foam as described herein, nor to the particular foam generator 122 that has been shown and described. Nor is the invention limited to the exemplary methods of operating the dispenser 10 that are described herein. All other methods of operating the dispenser 10 that would be apparent to a person skilled in the air are included within the scope of the invention.

Although the foamable liquid is preferably a hand cleaning fluid, such as hand soap or hand sanitizer, other types of foamable liquids could be used instead. The term "foamable liquid" is intended to encompass any flowable substance that is capable of foaming.

The fluid reservoir 12 could have any suitable construction, such as those disclosed in U.S. Pat. No. 7,984,825 to Ophardt et al., issued Jul. 26, 2011; U.S. Pat. No. 8,684,236 to Ophardt, issued Apr. 1, 2014; U.S. Pat. No. 5,373,970 to Ophardt, issued Dec. 20, 1994; U.S. Pat. No. 5,836,482 to Ophardt et al., issued Nov. 17, 1998; U.S. Pat. No. 8,113,388 to Ophardt et al., issued Feb. 14, 2012; and U.S. Pat. No. 9,682,390 to Ophardt et al., issued Jun. 20, 2017, which are incorporated herein by reference. The fluid reservoir 12 could also be omitted and replaced by any suitable source of foamable liquid, including for example a supply line that draws the foamable liquid from a remote source.

Any suitable construction for mounting the piston chamber forming element 24 to a dispenser housing could be used, including for example those shown in U.S. Pat. No. 10,242,301 to Ophardt et al., issued Mar. 26, 2019; U.S. Pat. No. 7,984,825 to Ophardt et al., issued Jul. 26, 2011; U.S. Pat. No. 8,684,236 to Ophardt, issued Apr. 1, 2014; U.S. Pat. No. 5,373,970 to Ophardt, issued Dec. 20, 1994; U.S. Pat. No. 5,836,482 to Ophardt et al., issued Nov. 17, 1998; U.S. Pat. No. 8,113,388 to Ophardt et al., issued Feb. 14, 2012; and U.S. Pat. No. 9,682,390 to Ophardt et al., issued Jun. 20, 2017, which are incorporated herein by reference.

The invention is not limited to the particular foam generator 122 that has been shown and described. Rather, any suitable arrangement for generating foam could be used, including for example those disclosed in U.S. Pat. No. 7,303,099 to Ophardt, issued Dec. 4, 2007; U.S. Pat. No. 8,272,539 to Ophardt et al., issued Sep. 25, 2012; U.S. Pat. No. 8,733,596 to Ophardt et al., issued May 27, 2014; U.S. Pat. No. 9,573,152 to Ophardt et al., issued Feb. 21, 2017; and U.S. Pat. No. 10,105,018 to Jones et al., issued Oct. 23, 2018, which are incorporated herein by reference.

The invention is not limited to the one-way foam outlet valve 74 as shown and described, and in some embodiments of the invention the one-way foam outlet valve 74 may be omitted entirely.

The invention is not limited to any particular structure for effecting axial movement of the piston forming body 22 relative to the piston chamber forming element 24. Rather, any suitable structure for effecting axial movement of the piston forming body 22 relative to the piston chamber forming element 24 could be used, including for example those disclosed in U.S. Pat. No. 8,272,539 to Ophardt et al., issued Sep. 25, 2012; U.S. Pat. No. 10,242,301 to Ophardt et al., issued Mar. 26, 2019; U.S. Pat. No. 7,984,825 to Ophardt et al., issued Jul. 26, 2011; U.S. Pat. No. 8,684,236 to Ophardt, issued Apr. 1, 2014; U.S. Pat. No. 5,373,970 to Ophardt, issued Dec. 20, 1994; U.S. Pat. No. 5,836,482 to Ophardt et al., issued Nov. 17, 1998; U.S. Pat. No. 8,113,388 to Ophardt et al., issued Feb. 14, 2012; and U.S. Pat. No. 9,682,390 to Ophardt et al., issued Jun. 20, 2017, which are incorporated herein by reference.

Any type of sensor 148 for determining or estimating the concentration of ozone could be used. For example, the sensor 148 could be configured to detect electromagnetic radiation generated by the corona discharge. The amount of electromagnetic radiation generated over time, and the wavelength(s) of the radiation, can be used to calculate or estimate the amount of ozone that has been generated by the corona discharge. Other types of sensors 148 could also be used, including for example sensors 148 that directly sense a concentration of ozone in the ozone generating chamber 134 or in the air compartment 110, or that sense a parameter that can be used for estimating or calculating the concentration of ozone in the ozone generating chamber 134 or in the air compartment 110. Alternatively, the sensor 148 could be omitted altogether.

The term "air" as used herein is intended to refer broadly to both atmospheric air and modified forms of air, such as ozonated air.

The invention is not limited to the particular configuration of the controller 136 as described herein. Rather, any suitable configuration that provides the desired functionality could be used. For example, in an alternative arrangement the controller 136 could adjust the amount of ozone that is generated based on feedback from a sensor 148 that senses the concentration of ozone in the foam itself, rather than in the air compartment 110 or the ozone generating chamber 134.

Although this disclosure has described and illustrated certain preferred embodiments of the invention, it is to be understood that the invention is not restricted to these particular embodiments. Rather, the invention includes all embodiments which are functional, electrical, chemical or mechanical equivalents of the specific embodiments and features that have been described and illustrated herein.

We claim:

1. A dispenser for dispensing ozone containing foam, the dispenser comprising:
   an ozone generating chamber having an air inlet in communication with a source of air and an air outlet, the ozone generating chamber containing a corona discharge generator that generates a corona discharge to produce: (a) ozonated air, by converting oxygen in the air into ozone, and (b) an ionic wind that draws the air from the air source into the ozone generating chamber through the air inlet, and expels the ozonated air from the ozone generating chamber through the air outlet;

a foam generator that receives the ozonated air expelled from the ozone generating chamber and mixes the ozonated air with a foamable liquid to generate the ozone containing foam;

a discharge outlet for discharging the ozone containing foam;

an air compartment that is in fluid communication with the air outlet for receiving the ozonated air from the ozone generating chamber, the air compartment in fluid communication with the foam generator for delivering the ozonated air from the air compartment to the foam generator;

a reservoir containing a supply of the foamable liquid;

a liquid pump for delivering the foamable liquid from the reservoir to the foam generator; and an air pump for delivering the ozonated air from the air compartment to the foam generator;

wherein the dispenser comprises a piston forming body and a piston chamber forming element;

wherein the piston forming body is slidable along a piston axis relative to the piston chamber forming element between an extended position and a retracted position;

wherein the piston chamber forming element has an air chamber forming portion that defines an air chamber;

wherein the piston forming body has an air displacement portion that is received within the air chamber;

wherein the air compartment is at least partially defined between the air displacement portion and the air chamber forming portion; and wherein axial movement of the air displacement portion relative to the air chamber forming portion during a dispensing stroke decreases the volume of the air compartment, which forces at least some of the ozonated air from the air compartment into the foam generator;

the dispenser further comprising a one-way air inlet valve that allows atmospheric air to enter the air compartment through the one-way air inlet valve, and that prevents the air from exiting the air compartment through the one-way air inlet valve;

wherein axial movement of the air displacement portion relative to the air chamber forming portion during a recharging stroke increases the volume of the air compartment, which generates a vacuum within the air compartment that draws the atmospheric air into the air compartment through the one-way air inlet valve.

2. The dispenser according to claim 1, wherein the air moves through the ozone generating chamber in an air flow path from the air inlet to the air outlet;

wherein the corona discharge generator comprises a first electrode and a second electrode, the first electrode positioned upstream from the second electrode in the air flow path;

wherein the first electrode produces ions that are attracted to the second electrode; and wherein the ionic wind is generated by movement of the ions from the first electrode towards the second electrode.

3. The dispenser according to claim 2, further comprising a desiccant that is positioned between the air inlet and the first electrode;

wherein the first electrode and the second electrode provide air flow passages that allow air to flow past the first electrode and past the second electrode to generate the ionic wind;

wherein the first electrode and the second electrode each comprise a plurality of elongated electrode members; and wherein the air flow passages are defined between the elongated electrode members.

4. The dispenser according to claim 1, wherein the air pump selectively decreases a volume of the air compartment to force at least some of the ozonated air from the air compartment into the foam generator.

5. The dispenser according to claim 1, wherein the air compartment is the source of air that is in fluid communication with the air inlet; and wherein the ionic wind circulates air and ozonated air between the air compartment and the ozone generating chamber in an air flow path from the air compartment into the ozone generating chamber through the air inlet, and from the ozone generating chamber into the air compartment through the air outlet.

6. The dispenser according to claim 1, wherein the piston chamber forming element has a liquid chamber forming portion that defines a liquid chamber;

wherein the piston forming body has a liquid displacement portion that is received within the liquid chamber;

wherein a liquid compartment is at least partially defined between the liquid displacement portion and the liquid chamber forming portion;

the dispenser further comprising a one-way liquid inlet valve that allows the foamable liquid to enter the liquid compartment from the reservoir through the one-way liquid inlet valve, and that prevents the foamable liquid from exiting the liquid compartment through the one-way liquid inlet valve;

wherein axial movement of the liquid displacement portion relative to the liquid chamber forming portion during the recharging stroke increases a volume of the liquid compartment, which generates a vacuum within the liquid compartment that draws the foamable liquid from the reservoir into the liquid compartment through the one-way liquid inlet valve; and wherein axial movement of the liquid displacement portion relative to the liquid chamber forming portion during the dispensing stroke decreases the volume of the liquid compartment, which forces at least some of the foamable liquid from the liquid compartment into the foam generator.

7. The dispenser according to claim 6, wherein the liquid chamber forming portion comprises an inner wall of the piston chamber forming element, the inner wall having an inner surface and an outer surface;

wherein the liquid compartment is at least partially defined between the inner surface of the inner wall and the liquid displacement portion;

wherein the air chamber forming portion comprises an outer wall of the piston chamber forming element that is spaced radially outwardly from the inner wall;

wherein the air compartment is at least partially defined between the outer surface of the inner wall, the air displacement portion, and the outer wall; and wherein the ozonated air expelled from the air outlet into the air compartment is directed into a curved circulation path around the outer surface of the inner wall.

8. The dispenser according to claim 7, further comprising a one-way air outlet valve that allows the ozonated air to enter the foam generator from the air compartment through the one-way air outlet valve, and that prevents fluid from entering the air compartment from the foam generator through the one-way air outlet valve.

9. The dispenser according to claim 1, further comprising a sensor that senses a concentration of ozone in the ozone generating chamber or in the air compartment, or that senses a parameter for estimating or calculating the concentration of ozone in the ozone generating chamber or in the air compartment.

10. The dispenser according to claims 9, further comprising a controller that controls the corona discharge generator so that the concentration of ozone in the ozone generating chamber or in the air compartment is within a preselected range of concentrations.

11. The dispenser according to claim 1, wherein the dispenser is a hand cleaner dispenser for dispensing the ozone containing foam onto a person's hand and the ozone containing foam is a hand cleaning foam.

12. The dispenser according to claim 5, wherein the air moves through the ozone generating chamber in the air flow path from the air inlet to the air outlet;
   wherein the corona discharge generator comprises a first electrode and a second electrode, the first electrode positioned upstream from the second electrode in the air flow path;
   wherein the first electrode produces ions that are attracted to the second electrode; and
   wherein the ionic wind is generated by movement of the ions from the first electrode towards the second electrode.

13. The dispenser according to claim 12, wherein the first electrode and the second electrode provide air flow passages that allow air to flow past the first electrode and past the second electrode to generate the ionic wind.

14. The dispenser according to claim 13, wherein the first electrode and the second electrode each comprise a plurality of elongated electrode members; and
   wherein the air flow passages are defined between the elongated electrode members.

15. The dispenser according to claim 8, wherein the air moves through the ozone generating chamber in the air flow path from the air inlet to the air outlet;
   wherein the corona discharge generator comprises a first electrode and a second electrode, the first electrode positioned upstream from the second electrode in the air flow path;
   wherein the first electrode produces ions that are attracted to the second electrode;
   wherein the ionic wind is generated by movement of the ions from the first electrode towards the second electrode;
   wherein the first electrode and the second electrode provide air flow passages that allow air to flow past the first electrode and past the second electrode to generate the ionic wind;
   wherein the first electrode and the second electrode each comprise a plurality of elongated electrode members;
   wherein the air flow passages are defined between the elongated electrode members; and
   wherein the dispenser further comprises a desiccant that is positioned between the air inlet and the first electrode.

16. The dispenser according to claim 15, further comprising:
   a sensor that senses a concentration of ozone in the ozone generating chamber or in the air compartment, or that senses a parameter for estimating or calculating the concentration of ozone in the ozone generating chamber or in the air compartment; and
   a controller that controls the corona discharge generator so that the concentration of ozone in the ozone generating chamber or in the air compartment is within a preselected range of concentrations;
   wherein the dispenser is a hand cleaner dispenser for dispensing the ozone containing foam onto a person's hand and the ozone containing foam is a hand cleaning foam.

* * * * *